US008114381B2

(12) United States Patent
Perrin et al.

(10) Patent No.: US 8,114,381 B2
(45) Date of Patent: Feb. 14, 2012

(54) RADIOLABELED COMPOUNDS AND COMPOSITIONS, THEIR PRECURSORS AND METHODS FOR THEIR PRODUCTION

(75) Inventors: David M. Perrin, Vancouver (CA); Richard Ting, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 1212 days.

(21) Appl. No.: 10/589,220

(22) PCT Filed: Feb. 14, 2005

(86) PCT No.: PCT/CA2005/000195
§ 371 (c)(1),
(2), (4) Date: May 21, 2007

(87) PCT Pub. No.: WO2005/077967
PCT Pub. Date: Aug. 25, 2005

(65) Prior Publication Data
US 2008/0038191 A1    Feb. 14, 2008

Related U.S. Application Data

(60) Provisional application No. 60/544,163, filed on Feb. 13, 2004.

(51) Int. Cl.
*A61K 51/04*  (2006.01)
*A61K 51/06*  (2006.01)
*C07F 5/02*   (2006.01)
(52) U.S. Cl. .................. 424/1.89; 424/1.45; 424/1.57; 424/1.65; 424/1.69; 424/1.73
(58) Field of Classification Search .................. 424/1.41, 424/1.65, 1.69, 9.3; 548/302.7, 303.7, 304.1
See application file for complete search history.

(56) References Cited

OTHER PUBLICATIONS

Tomothy M. Shoup, Synthesis of Fluorine-18-labeled Biotin derivatives: Biodistribution and Infection localization, J. Nucl. Med, 1994, 35, 1685-1690.*
Walsh, et al., "Application of Silicon-Fluoride Chemistry to Fluorine-18 Labeling Agents for Biomolecules: A Preliminary Note", J. Labelled Cpd. Radiopharm, 1999, vol. 42, Suppl. 1, pp. S1-S4.
Ishiwata, et al., "A unique in vivo assessment of 4-[$^{10}$B] borono-L-phenylalanine in tumour tissues for boron neutron capture therapy of malignant melanomas using positron emission tomography and 4-borono-2-[$^{18}$F]fluoro-L-phenylalanine", Melanoma Research, 1992, vol. 2, pp. 171-179.
Ishiwata, et al., "4-Borono-2-[$^{18}$F]fluoro-D,L-phenylalanine: a Possible Tracer for Melanoma Diagnosis with PET", International Journal of Radiation Applications and Instrumentation. Part B, Nuclear Medicine and Biology, 1992, vol. 19, No. 3, pp. 311-318.
Schirrmacher, et al. "$^{18}$F-labeling of peptides by means of an organosilicon-based fluoride acceptor", Angew. Chem. Int. Ed, 2006, vol. 45, pp. 1-5.
Imahori, Y., et al., *Positron Emission Tomography-based Boron Neutron Capture Therapy Using Boronophenylalanine for High-Grade Gliomas: Part I*, Clinical Cancer Research, vol. 4, Aug. 1998, pp. 1825-1832.
Imahori, Y., et al., *Positron Emission Tomography-based Boron Neutron Capture Therapy Using Boronophenylalanine for High-Grade Gliomas: Part II*, Clinical Cancer Research, vol. 4, Aug. 1998, pp. 1833-1841.
Kabalka, G., et al., *The Development of Boron Neutron Capture Agents Utilizing Positron Emission Tomography*, Special publication Royal Society of Chemistry (Great Britain), vol. 253, (2000), Contemporary Boron Chemistry—Medicinal Applications, pp. 120-126.
Kabalka, G., et al., *Evaluation of Fluorine-18-BPA-Fructose for Boron Neutron Capture Treatment Planning*, The Journal of Nuclear Medicine, vol. 38, No. 11, Nov. 1997, pp. 1762-1767.
Nichols, T., et al., *Improved treatment planning for boron neutron capture therapy for glioblastoma multiforme using fluorine-18 labeled boronophenylaianine and positron emission tomography*, Med. Phys. vol. 29, No. 10, Oct. 2002, pp. 2351-2358.
Ting, et al., "Substituent Effects on Aryltrifluoroborate Solvolysis in Water: Implications for Suzuki-Miyaura Couplin: and the Design of Stable $^{18}$F-Labeled Aryltrifluoroborates for use in PET Imaging", J. Org. Chem., (2008), vol. 73 pp. 4662-4670.
Ting, et al., "Arylfluoroborates and Alkylfluorosilicates as Potential PET Imaging Agents: High-Yielding Aqueous Biomolecular $^{18}$F-Labeling", J. Am. Chem. Soc. (2005), vol. 127, pp. 13094-13095.
Ting, et al., "Toward [$^{18}$F]-Labeled Aryltrifluoroborate Radiotracers: In Vivo Positron Emission Tomography Imaging of Stable Aryltrifluoroborate Clearance in Mice", J. Am. Chem. Soc., (2008), vol. 130, pp. 12045-12055.
Ting, et al., "Capturing aqueous [$^{18}$F]-flouride with an arylboronic ester for PET: Synthesis and aqueous stability of a fluorescent [$^{18}$F]-labeled aryltrifluoroborate", Journal of Fluorine Chemistry, (2008), vol. 129, pp. 349-358.
Harwig, et al., "Synthesis and characterization of 2,6-difluoro-4-carboxyphenylboronic acid and a biotin derivative thereof as captors of anionic aqueous [$^{18}$F]-fluoride for the preparation of [$^{18}$F/$^{19}$F]-labeled aryltrifluoroborates with high kinetic stability", Tetrahderon Letters, (2008), vol. 49, pp. 3152-3156.
Li, et al., "Hydrolytic stability of nitrogenous-heteroaryltrifluoroborates under aqueous conditions at near neutral pH", Journal of Fluorine Chemistry (2009) vol. 130, pp. 377-382.
Supplemental European Search Report dated Mar. 26, 2010, corresponding to 05706491.7-2101/1723161 and PCT/CA2005000195.
Poole, et al., "Radiotracers in Fluorine Chemistry. Part IV.[1] Fluorine-18 Exchange between labelled Alkyfluorosilanes and Fluorides, or Fluoride Methoxides, of Tungsten$_{(VI)}$, Molybdenum, $_{(VI)}$, Tellurium$_{(VI)}$, and Iodine$_{(v)}$ †", J.C.S. Dalton, (1976), pp. 1557-1560.

(Continued)

*Primary Examiner* — Michael G Hartley
*Assistant Examiner* — Jagadishwar Samala
(74) *Attorney, Agent, or Firm* — Christie, Parker & Hale, LLP

(57) ABSTRACT

Positron emitting compounds and methods of their production are provided. The compounds have the formula: (F)m G (R)n wherein each R is a group comprising at least one carbon, nitrogen, phosphorus or sulfur atom and G is joined to R through said carbon, nitrogen, phosphorus or sulfur atom; G is silicon or boron; m is 2 to 5 and n is 1 to 3 with m+n=3 to 6 when G is silicon; m is 1 to 3 and n is 1 to 3 with m+n=3 to 4 when G is boron; and wherein the compound further comprises one or more counterions when the above formula is charged; and wherein at least one F is 18F.

22 Claims, No Drawings

OTHER PUBLICATIONS

Shoup, et al., "Synthesis of Fluorine-18-Labeled Biotin Derivatives: Biodistribution and Infection Localization", The Journal of Nuclear Medicine, (1994), vol. 35, pp. 1685-1690.

Okarvi, "Recent Progress in Fluorine-18 labelled peptide radiopharmaceuticals", European Journal of Nuclear Medicine, (2001), vol. 28, pp. 929-938.

International Search Report dated Jun. 6, 2005, corresponding to PCT/CA2005/000195.

Walsh, J.C. et al., "Application of silicon-fluoride chemistry to fluorine-18 labeling agents for biomolecules: A preliminary note", Journal of Labelled Compounds and Radiopharmaceuticals, Jun. 1999, vol. 42, No. Suppl. 1 pp. Si-S4 (On Order).

Ishiwata, K. et al., "A unique in vivo assessment of 4-[$^{10}$B] borono-L-phenylalanine in tumour tissues for boron neutron capture therapy of malignant melanomas using positron emission tomography and 4-borono-2-[$^{18}$F]fluoro-L-phenylalanine", Melanoma Research, 1992, vol. 2, No. 3, pp. 171-179. (On Order).

Ishiwata, K. et al., "4-Borono-2-[$^{18}$F]fluoro-D,L-phenylalanine: a possible tracer for melanoma diagnosis with PET", International Journal of Radiation Applications and Instrumentation. Part B, Nuclear Medicine and Biology, 1992, vol. 19, No. 3, pp. 311-318 (On Order).

* cited by examiner

RADIOLABELED COMPOUNDS AND COMPOSITIONS, THEIR PRECURSORS AND METHODS FOR THEIR PRODUCTION

CROSS-REFERENCED TO RELATED APPLICATION(S)

This application is a National Phase Patent Application of International Application Number PCT/CA2005/000195, filed on Feb. 14, 2005, which claims the benefit of the filing date of U.S. Provisional Application No. 60/544,163, filed Feb. 13, 2004.

BACKGROUND OF THE INVENTION

Positron emitting compounds may be employed as markers and imaging agents because their presence and location are indicated by the annihilation of a nearby electron and the consequent emission of two oppositely oriented gamma rays. Gamma ray detectors can be used to detect the event and precisely determine its location.

Positron Emission Tomography (PET) relies upon the use of positron emitting radiolabeled tracer molecules and computed tomography to examine metabolic processes or to detect targets within the living body of a patient or experimental animal. Once injected, the tracer is monitored with a positron camera or a tomograph detector array. This technology can be more sensitive than scanning techniques such as magnetic resonance imaging (MRI), ultrasound imaging, or X-ray imaging. Some of the major clinical applications for PET are oncology, neurology, and cardiology.

Tracer molecules used in PET imaging are generally prepared by replacement of a group or atom in an unlabeled tracer with a radioisotope containing group or atom or by joining the tracer to a radioisotope containing atom (e.g. by chelation). Some common positron-emitting radioisotopes commonly used are: fluorine-18 ($^{18}F$); carbon-11 ($^{11}C$); nitrogen-13 ($^{13}N$); and oxygen-15 ($^{15}O$). In addition, $^{64}Cu$ has been appended to tracer molecules using copper chelation chemistry (Chen et al. Bioconjug. Chem. (2004) 15: 41-49).

$^{18}F$ is a particularly desirable radioisotope for PET imaging since it has a longer half-life than $^{11}C$, $^{13}N$ and $^{15}O$, readily forms covalent bonds, and has a short range beta+ emission that provides for high resolution in PET imaging. $^{18}F$ also does not suffer from a drawback associated with the use of $^{64}Cu$, whereby the copper may become sequestered by native proteins in a non-specific manner resulting in "streaking" of the PET image.

$^{18}F$ is not a naturally occurring isotope and is not found in fluorine or fluoride ions from natural sources. $^{18}F$ is only produced in nuclear reactions, typically by bombardment of an appropriate target in a cyclotron or proton accelerator. $^{18}F$ labeled tracer molecules are generally produced close to an accelerator facility. There are several facilities throughout the world that are able to produce $^{18}F$ and labeled tracers are routinely supplied from these facilities.

PET tracers often are or include, a molecule of biological interest (a "biomolecule"). Biomolecules developed for use in PET have been numerous. They can be small molecules as ubiquitous as water, ammonia and glucose or more complex molecules intended for specific targeting in the patient, including labeled amino acids, nucleosides and receptor ligands. Specific examples include $^{18}F$ labeled fluorodeoxyglucose, methionine, deoxythymidine, L-DOPA, raclopride and Flumazenil.

Several approaches for incorporating $^{18}F$ in biomolecules are described in the following references: Kuhnast, B., et al. (2004) J. Am. Chem. Soc., 15, 617-627; Garg, P. K., et al. (1991) Bioconj. Chem., 2, 44-49; Lee, B. C., et al. (2004) J. Am. Chem. Soc., 15, 104-111; Chen, X., et al. (2004) J. Am. Chem. Soc., 15, 41-49; Glaser, M., et al. (2004) J. Am. Chem. Soc., 15, 1447-1453; Toyokuni et al. Bioconjug. Chem. (2003) 14: 1253-9; and Couturier, O., et al. (2004) Eur. J. of Nuc. Med. and Mol. Imaging, 31, 1182-1206). These processes involve replacement of an existing group on the biomolecule with $^{18}F$. These methods are time consuming, thereby reducing PET image resolution as a result of nuclear decay. Also the fluorination conditions can adversely affect a biomolecule.

Walsh et al. in J. Labelled Cpd. Radiopharm. 42, Suppl. 1(1999) and Journal of Nuclear Medicine, Supp. S. 2000, 41 1098 described PET precursor compounds containing one $^{18}F$, two phenyl groups and a tertiary-butyl group each bonded to a silicon atom. The two phenyl and tertiary-butyl groups were required to provide hydrolytic stability. One of the phenyl groups included a thio-reactive or amine-reactive group for subsequent bonding to a biomolecule.

SUMMARY OF THE INVENTION

This invention is based, in part, on the realization that multiple F atoms may be joined to silicon. Thus, a greater number of $^{18}F$ atoms could be incorporated into a single tracer or, when a fluorinating agent employed contains natural F or $F_2$, a greater proportion of the resulting molecules will incorporate $^{18}F$. This enhances the density of positron emitters in the resulting product. Furthermore, the presence of multiple F atoms stabilizes a silicon moiety under physiological and other aqueous conditions and the presence of large alkyl or aromatic stabilizing groups (such as were employed by Walsh et al. [supra]) is not necessary.

This invention is also based on the realization that boron is an excellent F acceptor and may be employed as an alternative to silicon for fluorination with $^{18}F$. Boron containing moieties will accept from one to three $^{18}F$ atoms and are also stable under physiological and other aqueous conditions. In some circumstances, the stability of the B—$^{18}F$ bond is superior to the Si—$^{18}F$ bond. Also, boron is less reactive to glassware, glass storage vessels and delivery type devices than silicon.

Various embodiments of this invention provide a compound of the formula:

wherein each R is a group comprising at least one carbon, nitrogen, phosphorus or sulfur atom and G is joined to R through said carbon, nitrogen, phosphorus or sulfur atom; G is silicon or boron; m is 2 to 5 and n is 1 to 3 with m+n=3 to 6 when G is silicon; m is 1 to 3 and n is 1 to 3 with m+n=3 to 4 when G is boron; and wherein the compound further comprises one or more counterions when the above formula is charged; and wherein at least one F is $^{18}F$.

Other embodiments of this invention provide a method of preparing a positron emitting compound comprising fluorinating a compound of the formula

with $^{18}F$ to produce a compound of the formula:

wherein each L is the same or different and is a leaving group capable of being displaced by fluorine, R, G, m and n are as defined in any one of claims 1 to 16, q is 1 or 3 when G is boron and q is 2 or 3 when G is silicon, and wherein at least one F is $^{18}F$.

Various embodiments of this invention provide PET imaging compositions comprising a physiologically acceptable carrier or excipient and a positron emitting compound of this invention.

Various embodiments of this invention provide the use of a compound of this invention in the preparation of a positron emitting agent, for use in labeling and imaging, including PET imaging.

Various embodiments of this invention provide the use of a compound or composition of this invention in imaging of a living body.

Various embodiments of this invention provide a method of performing PET imaging of the body of a human or animal patient, comprising administering an effective amount of a PET imaging compound or composition of this invention to the patient. Also included is a method which comprises selecting from a panel of compounds, a compound comprising a boron or silicon fluorine acceptor moiety coupled to a desired biomolecule for fluorination with $^{18}F$, as well as fluorinating such a selected compound with $^{18}F$ to produce a compound of this invention having a desired biological activity or targeting capability within a patient's body. In particular embodiments, such a panel of compounds may be bonded to or otherwise associated with a surface or substrate to facilitate identification, localization or selection of a desired biomolecule. In a particular embodiment, each member of such a panel may comprise a different biomolecule coupled to a silicon containing fluorine acceptor as described herein, the silicon moiety being coupled to an appropriate substrate such as a glass or other silicate surface. In the latter embodiment, a desired compound may be obtained and simultaneously labeled with $^{18}F$ by eluting the selected panel member from the substrate using fluorination agent which displaces the silicon moiety from the substrate. In another embodiment, precursors labeled with boron that await fluorination are bound to a solid support that comprises an alcohol (eg. diol or triol) to afford boronic ester linkages. Such supports may include polysaccharides such as dextran, sephladex and cellulose.

DETAILED DESCRIPTION OF THE INVENTION

Compounds of this invention and products of the methods of this invention will contain at least one $^{18}F$ atom. $^{18}F$ is typically produced in a cyclotron using several alternative nuclear reactions (see Helus, F. et al. (1979) *Radiochemical Radioanalytical Letters* 38: 395-410). In some cases, a neon gas target is employed and $^{19}F_2$ is typically added to keep the radioisotope in an oxidized form. The $^{18}F$ product, with $F_2$ carrier is obtained in a gas form. In other cases, the target is $^{18}O$ enriched water or $^{18}O^{19}F$, $^{18}O_2$, in which case $^{18}F$ may be recovered as fluoride ion or as $^{18}F_2$. However, $^{19}F_2$ carrier and an inert carrier gas such as argon are often employed to recover $^{18}F_2$ in gas form or a water product containing $^{18}F$ ion is recovered. In some cases, $^{18}F$ (fluoride) is recovered from water by distillation or chromatography. While $^{18}F_2$ (or less reactive forms such as $^{18}F$-acetyl hypofluorite or $^{18}$-xenon difluoride in combination with carrier fluorine) can be used directly as a fluorination agent in electrophilic reactions, $^{18}F$ is often converted to a form suitable as an agent in aliphatic nucleophilic displacements or aromatic substitution reactions. In the latter forms, the $^{18}F$ may be combined with a metal ion complexing agent such as crown ether or a tetrabutyl ammonium salt, a triflate, or a positively charged counter ion (including $H^+$, $K^+$, $Na^+$, etc). When used in aqueous solution, fluoride ions must be accompanied by positively charged counterions and this can also be provided by complexing $^{18}F$ with large metal ions such as rubidium, cesium, potassium complexed by a cryptand (e.g. Kryptofix222™) or tetrabutyl ammonium salts.

This invention contemplates the use of any appropriate $^{18}F$ containing fluorination agent selected for the specific conditions to the nature of the leaving group molecule and the nature of the tracer or precursor molecule being fluorinated. As indicated above, fluorination will typically result in the presence of natural fluorine isotopes in addition to $^{18}F$ either by the presence of $^{19}F$ contaminants or $^{19}F$ carrier anions. Thus compounds of this invention may contain natural fluoride isotopes (e.g. $^{19}F$) in addition to $^{18}F$. Furthermore, any composition of this invention may comprise compounds containing at least one $^{18}F$ atom as well as identical or similar compounds in which no fluorine atom is $^{18}F$. Nevertheless, all compounds and compositions of this invention will include an $^{18}F$ atom.

Without limitation, specific examples of fluorination agents that may be employed are those described above as well as $H^{18}F$, $K^{18}F$, $KH^{18}F_2$, $^{18}F$-enriched metal fluorine salts, $^{18}F$-enriched salts of quaternary nitrogenous bases (such as $(Bu)_4NF$), and solutions thereof. Fluorination agents may be used in an appropriate solvent or cosolvent, including without limitation water, methanol, ethanol, THF, dimethylformamide (DMF), formamide, dimethylacetamide (DMSO), DMA, dioxane, acetonitrile, and pyridine.

A feature of this invention is that through the use of silicon and boron moieties, a single compound of this invention can contain multiple fluorine atoms. Depending upon the number of fluorine atoms that are incorporated, a compound of this invention may be charged or uncharged. When charged, compounds of this invention will additionally comprise one or more cationic counterions, which may be any cation, which will stabilize the charge. Without limitation, examples of such cations are hydrogen, potassium, sodium, etc. Often, the counterion is derived from the fluorinating agent. Compounds of this invention may also comprise additional anions which may also be derived from the fluorination reaction. Preferably, any anions present will be ones which do not effectively compete with the fluoride ion in nucleophilic displacement reactions. Preferred anions are hydroxide or carbonate.

Compounds of this invention are prepared by fluorinating a precursor compound with an $^{18}F$ source or an $^{18}F$ containing fluorination agent. Precursor compounds of this invention will comprise a silicon or boron atom to which one or more leaving groups are joined. A leaving group is any chemical group or moiety capable of being displaced by a fluorine atom. Many such leaving groups are known and may be selected according to the nature of the fluorination agent, reaction conditions, and the nature of the other side groups bonded to the silicon or boron atom. Selection of appropriate leaving groups for both boron and silicon moieties may be made based on the current knowledge and literature concerning formation of boron-fluorine complexes and silyl fluoride complexes with $^{19}F$.

Methods by which organo-B-$^{19}F_3$ "ate" complexes are produced are well understood in the art. For example, boronic acids including aryl, olefinic, alkynyl and aliphatic linked boronic acids are readily converted to their corresponding "ate" complexes—e.g. trifluoroborate salts. These reactions are routinely used in synthetic organic chemistry. Organoboron compounds have also been synthesized with the expressed purpose of reacting with fluoride to form stable boron-fluoride complexes that produce a fluorescent or colorimetric signal. (see, for example, Vos de Wael, E., et al. (1977) *Rucueil, Journal of the royal netherlands chemical* society, 96, 306-309; Batey, R. A., et al. (2001) *Tet. Lett.*, 42, 9099-9103; McCusker, P. A. et al. (1957) *J. Am. Chem. Soc.*, 79, 5185-5188; Muetterties, E. L. (1958) *J. Am. Chem. Soc.*, 80, 4526-4528; McCusker, P. A., et al. *J. Am. Chem. Soc.*, 77, 4253-4255; Frohn, H.-J., et al. (2000) *J. Organomet. Chem.*, 598, 127-135; Vedejs, E., et al. (1995) *J. Org. Chem.*, 60, 3020-3027; Matteson, D. S. (1989) *Chem. Rev.*, 89, 1535-1551; Sutton, C. H., et al. (1992) *Inorg. Chem.*, 31, 4911-4916; Wright, S. W., et al. (1994) *J. Org. Chem.*, 59, 6095-6097; Sole, S. et al. (2004) *Chem. Comm.*, 1284-1285; DiCesare, N., et al. (2002) *Analytical biochemistry*, 301, 111-116; Cooper, C. R., et al. (1988) *Chem. Comm.*, 1365-1366; Stones, D., et al. (2004) *Chem. Eur. J.*, 10, 92-100; and Secor, K. E., et al. (2004) *Org. Lett.*, 6, 3727-3730). These methods may be readily adopted for incorporation with use of $^{18}F$.

The preparation of silyl fluorides is also well understood in the art. For example, a tri-substituted silyl group may be introduced onto a heteroatom, typically oxygen. Treatment with H-$^{19}F$, K-$^{19}F$, or KH-$^{19}F_2$ results in cleavage of the Si—O bond and results in a tri-organosilylfluoroide. Others have made use of RO—Si(bis-organo)—OR linkages that when fluorinated result in a bis-organodifluorosilane. The preparation of tetrafluoroalkylsilicates (RSi—$^{19}F_4^{-1}$), which are stable to aqueous treatment (since they are crystallized from water) is also known. These are synthesized by $^{19}F$ fluorination of corresponding trialkoxy/aryloxysilanes or tetralkoxy/aryloxy silicates (Kim, J., et al. (2004) *J. Org. Chem.*, 69, 3008-3014; Fang, S., et al. (2003) *Nucl. Acids Res.*, 31, 708-715; Lin, W. C., et al. (1991) *J. Org. Chem.*, 56, 6850-6856; Tacke, R., et al. (1993) *Inorg. Chem.*, 32, 2761-2766; Tacke, R., et al. (1998) *Organometallics*, 17, 3670-3676; Johnson, S. E., et al. (1989) *Inorg. Chem.*, 28, 3190-3198; Cruz-Aguado, J. A., et al. (2004) *J. Am. Chem. Soc.*, 126, 6878-6879; Bartzoka, V., et al. (1998) *Langmuir*, 14, 1887-1891; Jitchum, V., et al. (2001) *Tetrahedron*, 57, 3997-4003; and Keana, J. F. W., et al. (1986) *J. Org. Chem.*, 51, 1641-1644).

Leaving groups for use in this invention include any groups joined to the silicon or boron atom having an appropriate adjacent atom or atoms to provide for substitution by a fluorine atom. Such leaving groups include halogens, including Cl, Br and I, cyclic sulfates, mesylates and tosylates, nitro and trimethylammonium groups (e.g. see Schyler, D. J., (2004) Annals *Academy of Medicine* 33:146-154 and references cited therein for summary). Particular embodiments of this invention as exemplified herein employ leaving groups such as alkoxy groups in which the atom adjacent the silicon or boron atom is oxygen. Thus, use of particularly convenient leaving groups for use in this invention are groups which form alkyl or aromatic ether substituents on silicon or boron moieties used in this invention.

The relative thermodynamic energies of the B—O bond (128 kcal mol$^{-1}$), the B—F (146.5±13 kcal mol$^{-1}$) bond, the Si—O bond (108 kcal mol$^{-1}$) and the Si—F bond (135 kcal mol$^{-1}$) are known (see: Inorganic Chemistry—Principles of Structure and Reactivity, Appendix section: A21-24, Fourth Edition by J. E. Huheey, E. A. Keiter, and R. L. Keiter, Harper Collins College Publishers 1993). Replacement of two B—O bonds for two B—F bonds will generate approximately 39 kcal mol$^{-1}$ in net energy, which will favor the fluorinated product. Likewise, replacement of three Si—O bonds for three Si—F bonds will generate approximately 81 kcal mol$^{-1}$ in net energy, which will favor the fluorinated product.

Substituents of the boron and silicon atoms in compounds of this invention and such substituents additional to the leaving groups of compounds used in the methods of this invention (R in the formulae herein) may be any chemical group or moiety providing that the atom adjacent the silicon or boron molecule is carbon, nitrogen, phosphorous or sulfur. Preferably, the adjacent molecule is carbon or nitrogen, more preferably carbon. Aside from this limitation, any such substituent may be any moiety which may be joined to a silicon or boron atom, regardless of size or makeup. For compounds of this invention suitable for use as a PET imaging agent, one such substituent will be a "biomolecule" as contemplated herein and within the art concerning PET imaging agents. Thus, while R may be any aliphatic or aromatic moiety, including such moieties comprising heteroatoms, imaging agents of this invention will be ones in which at least one R substituent is a biomolecule as termed herein.

While biomolecules in PET imaging agents in the prior art included water, for the purposes of this invention, the term "biomolecule" means a molecule, compound or composition of medical, physiological or scientific significance, analog or derivative thereof that is compatible with a biological system or which possess biological activity. Biomolecules may be delivered into a human or animal and include biomolecules that become localized at particular places in the organism. Examples include sugars, amino acids, nucleic acids, nucleotides, nucleosides, peptide hormones (steroid and non-steroid), antibodies, aptamers and oligonucleotides, proteins, peptides, oligonucleotides, lipids, hormones, drugs (synthetic drugs and natural products), polysaccharides, liposomes, micelles, microsomes, magnetic particles, metal chelators, oligoribonucleotides, oligonucleotides and related analogs bearing modifications in the backbone, nucleobase, or phosphate linker regions that enhance stability or modulate specificity, peptidomimetics, dendrimers, drug delivery agents, nanotubes, fullerenes, virus particles, and other targeting molecules (e.g. cancer targeting molecules). Specific examples include, but not limited to, insulin, somatostatin, somatotropin, somatomedin, adrenocorticotropic hormone, parathormone, follicle stimulating hormone, luteinizing hormone, epidermal growth factor, thyroid stimulating hormone, thyroid stimulating hormone releasing hormone, luteinizing hormone releasing hormone, vasopressin, bombesin, endothelin, gonadotropins, gonadotropin releasing hormone, antiflamin I&II, NLE-antiflamin II, brain natriureitic peptide, calcitonin, corticotropin releasing peptide, oxytocin, calpain inhibitor peptide, alpha-CGRP, corticotropin releasing factor, galanin, growth hormone releasing factor, guanylin, alpha-helical corticotropin releasing factor, laminin, alpha-melanocyte stimulating hormone, platelet derived growth factor, neuromedin, neurotensin, pancreatic polypeptide, pentagastrin, peptide-YY, pituitary adenylate cyclase activating peptide, secretin, thyrotropin releasing hormone, urocortin, vasoactive intestinal peptide, vasopressin, vascular endothelial growth factor, apamin, bungarotoxin, calciceptin, charybdotoxin, cobrotoxin, conotoxin, dendrotoxin, melittin, neuropeptide-Y, imperatoxin, taycatoxin, inhibin, insulin-like growth factor, prolactin, melanin stimulating hormone, melanin concentrating hormone, substance-P, tachykinin, angiotensin, antibodies of general structural classes of IgG, IgM, IgE, IgA, as well as single-chain, monoclonal, and recombinant forms used for current and anticipated imaging, diagnostic, and therapeutic applications. Specific targets that can be recognized by antibodies comprise without limitation: melanoma cell, melanoma specific antigen, myelin basic protein, breast cancer specific tumor markers such as Her2-Neu and Brc-Abl, alpha-fetoprotein, human chorionic gonadotropin, prostate specific antigen, prostate specific membrane antigen, epidermal growth factor receptors, fibroblast growth factor receptor, insulin receptor. Other examples are antibodies approved for use in therapy: Herceptin (Amgen), Erbitux (Imclone). Polymers containing nucleobases and nucleotides including RNA, DNA, and PNAs and various synthetic derivatives thereof that reflect modification of the sugar, internucleoside linkage (backbone) and nucleobase portions are also contemplated. Oligonucleotides that can be used for imaging, for example: antisense oligonucleotides that target mRNA of genes implicated in the disease state, siRNA or RNAi molecules that target mRNA via RNA silencing, and aptamer structures which represent a diverse class of folded nucleic acid structures that target protein or glycoforms of proteins or both, or folded RNA structures. Further examples are aptamers approved for clinical use or those intended for clinical and diagnostic use such as Macugen (Eyetech) and aptamers that are used in the context of surface arrayed aptamers for diagnostic purposes, oligosaccharides of both synthetic and natural origin that are found on the surface of cellular receptors or can mimic the glycoforms of cellular receptors and proteins. Other saccharide components in synthetic glycoforms are sialic acid, mannose, fucose, N-acetyl-glucosamine, N-acetyl-mannosamine, maltose, galactose and N-acetyl-galactosamine, small to mid-size molecular weight ligands for proteins comprise various classes of compounds, for example: porphyrins, lectins, lipids, steroids, barbiturates, taxanes, terpenes, terpenoids, canabinoids, opioids, nucleosides, purines, pyrimidines, heteroaromatics, quinolines, biogenic amines, amino acids, indole-alkaloids, topane alkaloids, statins, enzyme inhibitors, nonsteroidal anti-inflammatory agents, monosaccharides, folates, derivatives of folate, methotrexate, derivatives of methotrexate, trexates, vitamins, growth hormone, VEGF, EGF, an antibody, a breast cancer antigen specific antibody, a prostate cancer antigen specific antibody, a melanoma antigen specific antibody, a ligand, a RGD-motif ligand recognizing a matrix metalloprotease, an aptamer, an aptamer recognizing a cell surface protein, folic acid, a folic acid derivative and a methotrexate.

Embodiments of this invention may include methods involving the $^{18}F$ fluorination of compounds otherwise ready for use as markers or imaging agents and the $^{18}F$ containing compounds derived therefrom. Thus, the compounds subjected to fluorination may already include a desired biomolecule for PET imaging purposes. However, preferred embodiments of this invention involve the formation of a precursor molecule, which may include such a biomolecule, prior to fluorination and fluorination with $^{18}F$ is the last step in the process prior to preparation of the compound for administration to a patient. Use of the silicon or boron containing moieties described herein facilitates the latter process. Thus, a desired PET imaging agent may be pre-formed with the silicon or boron moiety containing one or more leaving groups. The latter compound is then subjected to $^{18}F$ fluorination whereby the leaving groups are substituted with the radioactive fluorine that in the preferred embodiment will also contain the naturally occurring $^{19}F$. The compound may thus be used immediately in preparation of a PET imaging composition for immediate administration to the patient. A feature of this invention is that the boron and silicon moieties bonded to $^{18}F$ may be designed to be stable in aqueous solutions and in particular, at pH 3.0-9.0, more particularly, at pH 4.0-8.0 and most particularly physiological pH (about pH 7.4). Boron containing moieties of this invention readily provide stability in many embodiments and silicon containing embodiments of this invention with two or more fluorine atoms attached provide such stability in the absence of large steric side groups, as required in the prior art.

In some embodiments of this invention, the fidelity of activity of a desired imaging agent may be established prior to fluorination. In addition, compositions comprising biological molecules may be prepared and fluorinated with minimal purification in view of the ease by which the boron and silicon moieties used in this invention are fluorinated. In the preferred embodiments of this invention that may involve nanoliter reaction vessels or precursors attached to either glass or diol surfaces respectively for silicon or boron, no additional purification would be required. In another preferred embodiments of this invention, the reagents and conditions necessary for fluorination need not be applied to a moiety comprising a biomolecule, thereby risking alteration or denaturation of the biomolecule. The biomolecule may be joined to the $^{18}F$ fluorinated moiety subsequent to fluorination.

Having regard to the foregoing, substituents on a silicon or boron atom in compounds for use in this invention may include linking groups or reactive groups designed to facilitate subsequent addition of a biomolecule. Linking groups may include aliphatic or aromatic molecules designed to insulate the biomolecule from the silicon or boron atom by an appropriate distance or to ensure that appropriate atoms are adjacent the silicon or boron atom to facilitate the fluorination process. Groups which facilitate subsequent addition of a biomolecule are well known in the art and may include moieties which readily form a bond to a selected biomolecule, a variety of such groups being known in the art. These include thiol and amine reactive groups and other such groups which may be useful for joining a compound of this invention to functionalities on biomolecules including hydroxide, carboxylic acid, amine, sulfhydryl groups, etc. Contemplated herein, is the joining of a compound of this invention to a biomolecule through bonds other than covalent bonds. Thus, groups, which provide for ionic, hydrophobic and other non-covalent to a biomolecule are contemplated.

Where the silicon or boron containing moiety has be fluorinated with $^{18}F$, subsequent joining of the moiety via a substituent to a biomolecule may be carried out. This allows biomolecules that would denature during fluorination to become $^{18}F$-labeled. For example, one may first fluorinate a small molecule boronic acid or ester, converting this to the "ate" complex. The activated "ate" complex may then be conjugated to a biomolecule, resulting in a $^{18}F$-boron-biomolecule moiety.

General approaches to direct chemical modifications of biomolecules for the addition and substitution of modifying groups are known in the art. For example, chemical modification of proteins is described in G. E. Means and R. E. Feeney, *Bioconjugate Chemistry* 1990 1: 2-12. Chemical modification of large molecules including DNA, RNA are described in A. S. Boutourine, et al. *Bioconjugate Chemistry* 1990 1: 350-56. Chemical modification of oligosaccharides is described in S. J. Wood, et al. *Bioconjugate Chemistry* 1992 3: 391-6.

A biomolecule that already has a boronic acid or ester, or a molecule that contains a silyl group may require some modification with a fluoride acceptor structure to allow fluorination at the acceptor site while not altering the pre-existing boronic acid or silyl group, which may be necessary for the tracer's bioactivity. For example, some protease inhibitors exist that contain either a boronic acid or a dialkyldihydroxysilyl group and some amino acid analogs have been developed that are "borane amino acids", having the CH at the alpha position replaced with a boron atom.

Biomolecules that are small hydrophobic molecules, or molecules containing a carbon-palladium, carbon-rhodium and carbon-ruthenium bonds, where the metal is found in a formal oxidation state of 0 may require modification to provide attached fluorinated moieties. Biomolecules that require the presence of particular metal cations for activity may require more handling if the metal cations precipitate fluoride or prevent fluorination at boron or silicon. These metal cations may include silver, strontium, lead, calcium and magnesium. However, if the metal cation is not required for bioactivity of the tracer, then fluorination may proceed unimpeded in the absence of the cation or upon removal of the cation. Addition of the metal cation following fluorination is possible provided that a) its absence during the fluorination did not result in denaturation of the biomolecule b) that subsequent addition of the cation restores the biomolecule to its normal or active state and c) the addition of the metal cation does not promote defluorination at boron or silicon. Such biomolecules that may require consideration in terms of the presence of metal cations are envisaged to be largely limited to enzymes and antibodies containing the aforementioned metal cations.

Precursor molecules may have the following general structure.

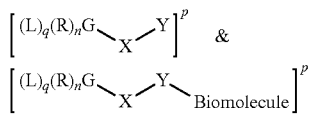

Where

G is boron, q=0 to 3; n=0 to 2; q+n=2 to 3 and p represents the charge of the molecule.

Each L may be the same or different and is a suitable leaving group that can be displaced by fluorine upon treatment with a fluorinating agent. For example, each L may be any single, saturated or unsaturated, branched, or linear combination of carbons, hydrocarbons, alkoxides (—OR), hydroxides (—OH) or equivalently alcohols (HOR) or water ($H_2O$), nitrogen (—$NH_2$, —NHR, —$NR_2$, —$NHR^+$, —$NR_2^+$, —$NH_3^+$, —$NH_2R^+$, —$NR_3^+$) phosphorus (—$PH_2$, —PHR, —$PR_2$, —$PHR^+$, —$PR_2^+$, —$PH_3^+$, —$PH_2R^+$, —$PR_3^+$), sulfur (—SH, —SR), sulfone (—SOR), or sulfoxide (—$SO_2R$) liganded atoms (where R is any chemical group). L may also be either Cl, Br or I. When q=0, then q represents a covalently unoccupied pole in the trigonal planar representation of boron which can be occupied by an $^{18}F$ fluorine atom. L may also be an alkylether group that leaves as either an alkoxide or as an alcohol or any other leaving group suitable for boron moieties described herein. Multiple L groups may be linked together to form a bi or tridentate ligand to boron, for example, $^-$O—Z—O$^-$ (where Z is a saturated or unsaturated, optionally substituted carbon chain, for example in a particular embodiment, Z may be -$CMe_2$-$CMe_2$-).

X may be absent, or may be an optionally substituted or unsubstituted; linear, branched, or cyclic; saturated or unsaturated group that links G to Y. X may incorporate groups of varying composition that include any composition of alkyl chains, aryl rings, amides, esters, ethers, thioethers, sulfoxides, sulfones, amines, heterocycles with varying compositions of C, N, H, S, O, Cl, Br, I, F, into an optionally substituted, linear or branched, saturated or unsaturated alkyl chain. X may contain an alkyl, alkenyl, alkynyl, or aromatic group that links to G. The carbon chain of X may be optionally interrupted by one or more O, N, S, P, or Si atoms in some.

Y may be a group that forms a bond to a biomolecule under suitable conditions. Y may contain an electrophilic activating group, for example, a carbonyl or a phosphate group, and may react with a nucleophile on the biomolecule, for example, a nitrogen or sulfur atom. Y may be, for example, an aromatic aldehyde, N-hydroxysuccinimidyl ester group, bromoacetyl, or maleimide. Y may be a suitable nucleophile activated in cases where the biomolecule contains electrophiles through which conjugation to Y may be achieved. Y may also be, for example, a haloacetyl, a haloketone, a sulfonylhalide, a primary amine, a secondary amine, a tertiary amine, an alkyl or aryl nitrile, an alkyl or aryl azide, an alkyl or aryl diazonium salt, an oxime, a hydroxylamine, a maleimide, an aminoxyl, a hydrazine, a hydrazide, a phosphate, a phosphoramidite, a phosphine or related trivalent phosphorous compounds, thiophosphate, phosphomorpholidate, phosphoimidazolide, and other activated phosphates. Y may be a sulfonate, sulfonylhalide, hydroxyl, thiol/mercaptan, thioacid, disulfide, primary alkylhalide, secondary alkylhalide, tertiary alkylhalide, arylhalide, aldehyde, ketone, carboxylic acid and related activated carboxylic acid forms (e.g. NHS esters, nitrophenylate esters, HOBt esters, acylpyridiniums, acylazides, and acylhalides), or any other precursor that can be linked to a biomolecule. Y may be linked for example, by nucleophilic substitution, electrophilic substitution, or pericyclic/electrocyclic reactions, and free radical additions.

Each R may independently be an aliphatic (alkyl) $(CH_2)_s$ (s$\geqq$ to 0) or aryl ($C_6H_5$) groups optionally interrupted by oxygen (—O—) groups or aryl ($C_6H_5$) groups substituted by 0 to 5 hydroxyl, alkyl, aryl, thio, thioether, amino, azo, hydrazino, ester, amide, carboxyl, carboxylate, amide, phosphate, sulfoxide and/or sulfonate groups. The saturated or unsaturated chain of each R may independently be optionally substituted by any number of hydroxyl, alkyl, aryl, thio, thioether, amino, azo, hydrazino, ester, amide, carboxyl, carboxylate, phosphate, sulfoxide and/or sulfonate groups. Alternatively, R may be a primary (NR), secondary ($NR_2$), or tertiary ($NR_3^+$) amine or imide, group (not excluding any nitrogen containing heterocycles), which may be substituted by any number of a hydroxyl, alkyl, aryl, thio, thioether, amino, ester, amide, carboxyl carboxylate, phosphate, sulfoxide and/or sulfonate groups.

The charge, p, of the compound will be variable depending on the valency of boron, the nature of the biomolecule, R, X, Y and L groups, and the pH. When the compound is charged, it will be associated with one or more counterions as required. Typically, p will be between −3 to 0. Charges on R, X, Y and L groups may also be associated with or serve as counterions, if required.

Precursor molecules may have the following general structure.

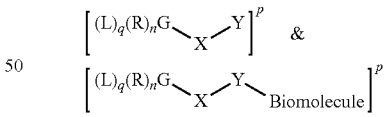

Where

G is silicon (Si), q=0 to 4; n=0 to 2; q+n=3 to 5 and p represents the charge of the molecule.

Each L may be the same or different and is a suitable leaving group that can be displaced by fluorine upon treatment with a fluorinating agent. For example, L may be any single, saturated or unsaturated, branched, or linear combination of carbons, hydrocarbons, alkoxides (—OR), hydroxides (—OH) or equivalently alcohols (HOR) or water ($H_2O$), nitrogen (—$NH_2$, —NHR, —$NR_2$, —$NHR^+$, —$NR_2$, $NH_3^+$, —$NH_2R^+$, —$NR_3^+$) phosphorus (—$PH_2$, —PHR, —$PR_2$, —$PHR^+$, —$PR_2^+$, —$PH_3^+$, —$PH_2R^+$, —$PR_3^+$), sulfur (—SH, —SR), sulfone (—SOR), or sulfoxide (—$SO_2R$) liganded atoms (where R is any chemical group). L may also be either Cl, Br or I. When q=0, then q represents covalently unoccupied poles in the representation of silicon which can be occupied by an $^{18}F$ fluorine atom (e.g. silicon in a porphyrin or porphyrin derivative). L may also be an alkylether group that leaves as either an alkoxide or as an alcohol, or another leaving group suitable for the silicon moiety as described here.

X may be absent, or may be an optionally substituted or unsubstituted; linear, branched, or cyclic; saturated or unsaturated group that links G to Y. X may incorporate groups of varying composition that include any composition of alkyl chains, aryl rings, amides, esters, ethers, thioethers, sulfoxides, sulfones, amines, heterocycles with varying compositions of C, N, H, S, O, Cl, Br, I, F, into an optionally substituted, linear or branched, saturated or unsaturated alkyl chain. X may contain an alkyl, alkenyl, alkynyl, or aromatic group that links to G. The carbon chain of X may be optionally interrupted by one or more O, N, S, or Si atoms.

Y may be a group that forms a bond to a biomolecule under suitable conditions. Y may contain an electrophilic activating atom, for example, a carbonyl or a phosphate group, and may react with a nucleophile on the biomolecule, for example, a nitrogen or sulfur atom. Y may be, for example, an aromatic aldehyde, N-hydroxysuccinimidyl ester group, bromoacetyl or maleimide. Y may be a suitable nucleophile activated in cases where the biomolecule contains electrophiles through which conjugation to Y may be achieved. Y may also be, for example, a haloacetyl, a haloketone, a sulfonylhalide, a primary amine, a secondary amine, a tertiary amine, an alkyl or aryl nitrile, an alkyl or aryl azide, an alkyl or aryl diazonium salt, an oxime, a hydroxylamine, a maleimide, a aminoxyl, a hydrazine, a hydrazide, a phosphate, a phosphoramidite, a phosphine or related trivalent phosphorous compounds, thiophosphates, phosphomorpholidates, phosphoimidazolides, and other activated phosphates, sulfonates, sulfonylhalides, hydroxyls, thiols/mercaptans, thioacids, disulfides, primary alkylhalides, secondary alkylhalides, tertiary alkylhalides, arylhalides, aldehydes, ketones, carboxylic acids and related activated carboxylic acid forms (e.g. NHS esters, HOBt esters, acylpyridiniums, azides, and halides), or any other precursor that can be linked to a biomolecule. Y may be linked to the biomolecule by nucleophilic substitution, electrophilic substitution, or pericyclic/electrocyclic reactions, and free radical additions.

Each R may be independently an aliphatic (alkyl) $(CH_2)_s$ ($s \geqq$ to 0) or aryl $(C_6H_5)$ groups optionally interrupted by oxygen (—O—) groups or aryl $(C_6H_5)$ groups substituted by 0 to 5 hydroxyl, alkyl, aryl, thio, thioether, amino, azo, hydrazino, ester, amide, carboxyl, carboxylate, phosphate, sulfoxide and/or sulfonate groups. The saturated or unsaturated chain of each R may independently be optionally substituted by any number of hydroxyl, alkyl, aryl, thio, thioether, amino, azo, hydrazino, ester, amide, carboxyl, carboxylate, phosphate, sulfoxide and/or sulfonate groups. Alternatively, R may be a primary (NR'), secondary (NR$_2$'), or tertiary (NR$_3$'$^+$) amine, imide, or imid group (not excluding any nitrogen containing heterocycles), which may be substituted by any number of a hydroxyl, alkyl, aryl, thio, thioether, amino, ester, amide, carboxyl carboxylate, phosphate, sulfoxide and/or sulfonate groups.

The charge, p, of the compound will be variable depending on the valency of silicon, the nature of the biomolecule, R, X, Y and L groups, and the pH. When the compound is charged, it will be associated with one or more counterions as required. Typically, p will be between −2 to 0. Charges on R, X, Y and L groups may also be associated with or serve as counterions, if required.

Radiolabeled compounds of this invention may also have one of the following structures.

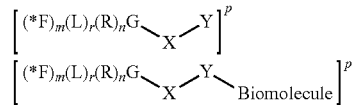

Where

G is boron (B), m=1 to 3; r=0 to 3, n=0 to 2; m+r+n=2 or 3 and p represents the charge of the molecule.

Each L may be the same or different and is a suitable leaving group that can be displaced by fluorine upon treatment with a fluorinating agent. Suitable leaving groups may be, for example, any single, saturated or unsaturated, branched, or linear combination of carbons, hydrocarbons, alkoxides (—OR), hydroxides (—OH) or equivalently alcohols (HOR) or water ($H_2O$), nitrogen (—$NH_2$, —NHR, —$NR_2$, —$NHR^+$, —$NR_2^+$, —$NH_3^+$, —$NH_2R^+$, —$NR_3^+$) phosphorus (—$PH_2$, —PHR, —$PR_2$, —$PHR^+$, —$PR_2^+$, —$PH_3^+$, —$PH_2R^+$, —$PR_3^+$), sulfur (—SH, —SR), sulfone (—SOR), or sulfoxide (—$SO_2R$) liganded atoms (where R is any chemical group). L may also be either Cl, Br or I. One embodiment may be, for example, n is zero, L is absent and boron is recognized as being tetravalent with the conjugate being considered an organotrifluoroborate. L may be any other leaving group suitable for the boron moiety as described herein.

X may be absent or may be an optionally substituted or unsubstituted; linear, branched, or cyclic; saturated or unsaturated group that links G to Y. X may incorporate groups of varying composition, for example, any composition of alkyl chains, aryl rings, amides, esters, ethers, thioethers, sulfoxides, sulfones, amines, heterocycles with varying compositions of C, N, H, S, O, Cl, Br, I, F, into an optionally substituted, linear or branched, saturated or unsaturated alkyl chain. X may contain an alkyl, alkenyl, alkynyl, or aromatic group that links to G. The carbon chain of X may be optionally interrupted by one or more O, N, S, P or Si atoms.

Y may be a group that forms a bond to a biomolecule under suitable conditions. Y may contain an electrophilic activating atom, (e.g. a carbonyl or a phosphate group), and may react with a nucleophile on the biomolecule (e.g. a nitrogen or sulfur atom). Y may be an aromatic aldehyde, N-hydroxysuccinimidyl ester group, bromoacetyl or maleimide. Y may be a suitable nucleophile activated in cases where the tracer contains electrophiles through which conjugation to Y may be achieved. In other embodiments, Y may be a haloacetyl, a haloketone, a sulfonylhalide, a primary amine, a secondary amine, a tertiary amine, an aromatic amine, an oxime, a hydroxylamine, a maleimide, a aminoxyl, a hydrazine, an alkyl or aryl diazonium salt, an alkyl or aryl nitrile, an alkyl or aryl azide, a hydrazide, a phosphate, a phosphoramidite, a phosphine, a H-phosphonate or related trivalent phosphorous compound, a thiophosphate, an activated phosphate (e.g. phosphomorpholidates and phosphoimidazolides, as well as other activated phosphates), a sulfonate, a sulfonylhalide, a hydroxyl, a thiol/mercaptan, a thioacid, a disulfide, a primary alkylhalide, a secondary alkylhalide, a tertiary alkylhalide, an arylhalide, an aldehyde, a ketone, a carboxylic acid or related activated carboxylic acid forms (e.g. NHS, HOBt esters, acylpyridiniums, azides, and halides) or any other precursor that can be linked to a biomolecule. The biomolecule may be linked to Y by nucleophilic substitution, electrophilic substitution, or pericyclic/electrocyclic reactions, and free radical additions.

Each R may be independently an aliphatic (alkyl) $(CH_2)_s$ (s=0 to 12) or aryl $(C_6H_5)$ groups optionally interrupted by oxygen (—O—) groups or aryl $(C_6H_5)$ groups substituted by 0 to 5 hydroxyl, alkyl, aryl, thio, thioether, amino, azo, hydrazino, ester, amide, carboxyl, carboxylate, phosphate, sulfoxide and/or sulfonate groups. The saturated or unsaturated chain of R may be optionally and independently substituted by any number of hydroxyl, alkyl, aryl, thio, thioether, amino, azo, hydrazino, ester, amide, carboxyl, carboxylate, phosphate, sulfoxide and/or sulfonate groups. Alternatively, R may be a primary (NR), secondary $(NR_2)$, or tertiary $(NR_3^+)$ amine or imide group (not excluding any nitrogen containing heterocycles), which may be substituted by any number of a hydroxyl, alkyl, aryl, thio, thioether, amino, ester, amide, carboxyl carboxylate, phosphate, sulfoxide and/or sulfonate groups.

The charge, p, of the compound will be variable depending on the valency of boron, the nature of the biomolecule, R, X, Y and L groups, and the pH. When the compound is charged, it will be associated with one or more counterions as required. Typically, p will be between −1 to 0. Charges on R, X, Y and L groups may also be associated or serve as with counterions, if required.

Radiolabeled compounds of this invention may also have one of the following structures.

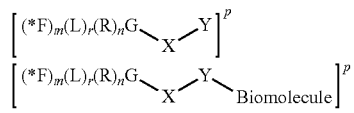

Where

G is silicon (Si), m=2 to 5; r=0 to 2; n=0 to 2, and 4; m+r+n=3 to 6 and p represents the charge of the molecule.

Each L may be the same or different and is a suitable leaving group that can be displaced by fluorine upon treatment with a fluorinating agent. Suitable leaving groups may be, for example, any single, saturated or unsaturated, branched, or linear combination of carbons, hydrocarbons, alkoxides (—OR), hydroxides (—OH) or equivalently alcohols (HOR) or water $(H_2O)$, nitrogen (—$NH_2$, —NHR, —$NR_2$, —NHR, —$NR_2^+$, —$NH_3^+$, —$NH_2R^+$, —$NR_3^+$) phosphorus (—$PH_2$, —PHR, —$PR_2$, —$PHR^+$, —$PR_2^+$, —$PH_3^+$, —$PH_2R^+$, —$PR_3^+$), sulfur (—SH, —SR), sulfone (—SOR), or sulfoxide (—$SO_2R$) liganded atoms (where R is any chemical group). L may also be Cl, Br, I, or any other leaving group suitable for the silicon moiety as described herein.

X may be absent or may be an optionally substituted or unsubstituted; linear, branched, or cyclic; saturated or unsaturated group that links G to Y. X may incorporate groups of varying composition, for example, any composition of alkyl chains, aryl rings, amides, esters, ethers, thioethers, sulfoxides, sulfones, amines, heterocycles with varying compositions of C, N, H, S, O, Cl, Br, I, F, into an optionally substituted, linear or branched, saturated or unsaturated alkyl chain. X may contain an alkyl, alkenyl, alkynyl, or aromatic group that links to G. The carbon chain of X may be optionally interrupted by one or more O, N, S, or Si atoms.

Y may be a group that forms a bond to a biomolecule under suitable conditions. Y may contain an electrophilic activating atom, (e.g. a carbonyl or a phosphate group), and may react with a nucleophile on the biomolecule (e.g. a nitrogen or sulfur atom). Y may be an aromatic aldehyde, N-hydroxysuccinimidyl ester group, bromoacetyl or maleimide. Y may be a suitable nucleophile activated in cases where the biomolecule contains electrophiles through which conjugation to Y may be achieved. In other embodiments, Y may be a haloacetyl, a haloketone, a sulfonylhalide, a primary amine, a secondary amine, a tertiary amine, an aromatic amine, an oxime, a hydroxylamine, a maleimide, a aminoxyl, a hydrazine, an alkyl or aryl diazonium salt, an alkyl or aryl nitrile, an alkyl or aryl azide, a hydrazide, a phosphate, a phosphoramidite, a phosphine, a H-phosphonate or related trivalent phosphorous compound, a thiophosphate, an activated phosphate (e.g. phosphomorpholidates and phosphoimidazolides, as well as other activated phosphates), a sulfonate, a sulfonylhalide, a hydroxyl, a thiol/mercaptan, a thioacid, a disulfide, a primary alkylhalide, a secondary alkylhalide, a tertiary alkylhalide, an arylhalide, an aldehyde, a ketone, a carboxylic acid or related activated carboxylic acid forms (e.g. NHS, HOBt esters, acylpyridiniums, azides, and halides) or any other precursor that can be linked to a biomolecule. Y may be linked to the biomolecule by nucleophilic substitution, electrophilic substitution, or pericyclic/electrocyclic reactions, and free radical additions.

Each R may be independently an aliphatic (alkyl) $(CH_2)_s$ (s=0 to 12) or aryl $(C_6H_5)$ groups optionally interrupted by oxygen (—O—) groups or aryl $(C_6H_5)$ groups substituted by 0 to 5 hydroxyl, alkyl, aryl, thio, thioether, amino, azo, hydrazino, ester, amide, carboxyl, carboxylate, phosphate, sulfoxide and/or sulfonate groups. The saturated or unsaturated chain of R may be optionally and independently substituted by any number of hydroxyl, alkyl, aryl, thio, thioether, amino, azo, hydrazino, ester, amide, carboxyl, carboxylate, phosphate, sulfoxide and/or sulfonate groups. Alternatively, R may be a primary (NR), secondary $(NR_2)$, or tertiary $(NR_3^+)$ amine, imide, or imid group (not excluding any nitrogen containing heterocycles), which may be substituted by any number of a hydroxyl, alkyl, aryl, thio, thioether, amino, ester, amide, carboxyl carboxylate, phosphate, sulfoxide and/or sulfonate groups.

The charge, p, of the compound will be variable depending on the valency of silicon, the nature of the biomolecule, R, X, Y and L groups, and the pH. When the compound is charged, it will be associated with one or more counterions as required. Typically, p will be between −2 to 0. Charges on R, X, Y and L groups may also be associated with or serve as counterions, if required.

In all preceding silicon embodiments particular R groups may be aryl, amino, methyl, phenyl, aminophenyl, aminomethylphenyl, alkoxymethylphenyl, a porphyrin, a porphyrin derivative and a biomolecule and particular L groups may be —OH, —O⁻, O-alkyl, O-aryl, pinacol, O-pyridyl, O-nitrophenyl, a silanized silicate, a triol presenting saccharide, a triol presenting silicate, and alcohol presenting solid supports.

In all preceding boron embodiments particular R groups may be aryl, amino, methyl, phenyl, aminophenyl, aminomethylphenyl, alkoxymethylphenyl, and a biomolecule and particular L groups may be —OH, O-alkyl, O-aryl, pinacol, O-pyridyl, O-nitrophenyl, diol presenting saccharides, and alcohol presenting solid supports.

Examples of the preparation of six kinds of precursor compounds that have appropriate chemical functionality for reacting with reactive sites on various biomolecules and examples of the synthesis are shown immediately below. The boron moiety of these precursors may be easily fluorinated with $^{18}F$, as described above.

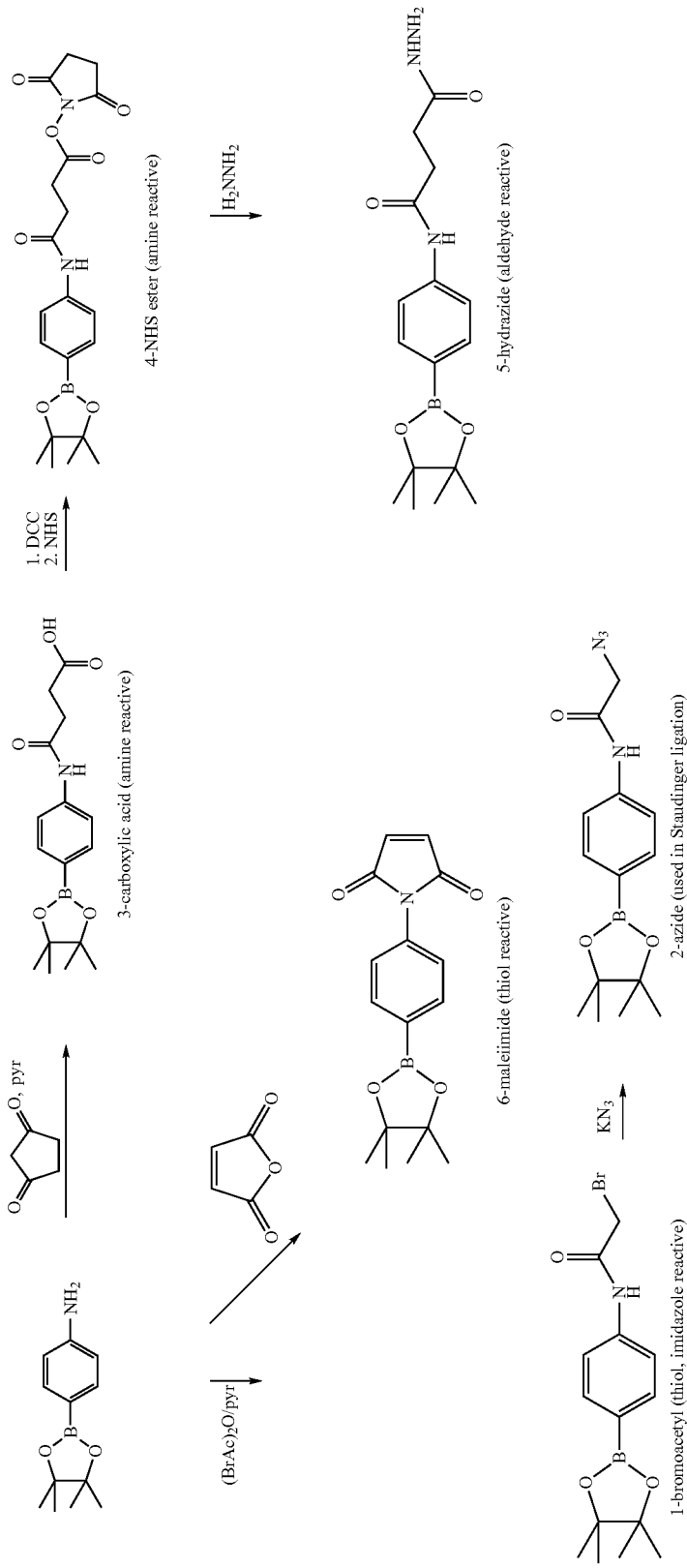

The following reaction scheme illustrates a portion of a synthetic route taken in the synthesis of a precursor molecule containing a boronic ester.

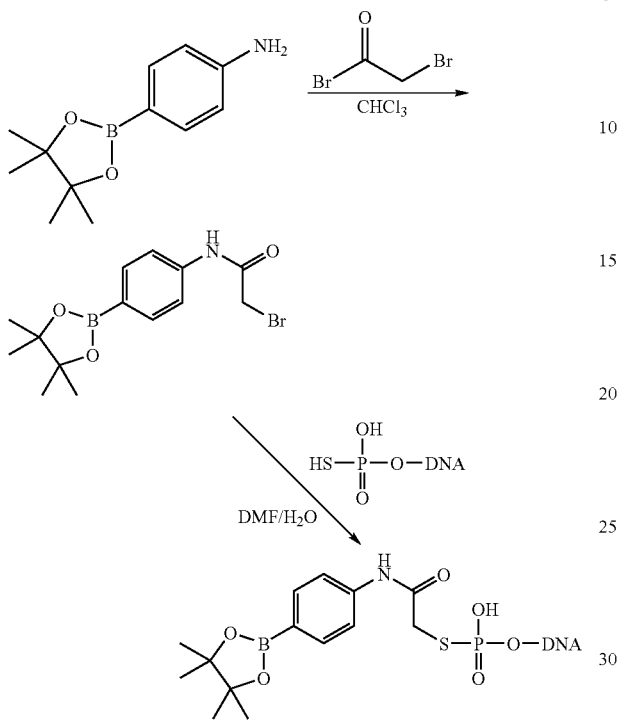

The scheme immediately below shows two biotin molecules (ligand for avidin) covalently modified with Fluoride acceptors (silicon and boron) that are prepared by standard coupling of the biotin-acid chloride and the corresponding commercially available amine.

Following labeling, excess $^{18}$F may be sequestered by addition of other components, for example, sliver salts, silicates or silanes, and other activated silicon-derived molecules, boronic esters or boronic acids, such that these additives react to complex free fluoride and where the complexation reaction is then removed by extraction, precipitation, gel-permeation, or other purificative/separative process.

As shown in Scheme A below, the composition of $^{18}$F-linker-tracer may be formed either via the preformation of the linker-tracer compound followed by reaction with a $^{18}$F-fluorinating source, or by the preformation of the $^{18}$F-linker compound followed by reaction with the tracer. The former method provides 1) the ability to prepare, purify, and analyze the precursor conjugate in bulk to ensure effective coupling and retain bioactivity prior to labeling and 2) the ability to minimize reaction steps following the incorporation of radiolabel, a consequence that is desirable with regard to both safety issues in handling the material and the relatively short half-life of $^{18}$F.

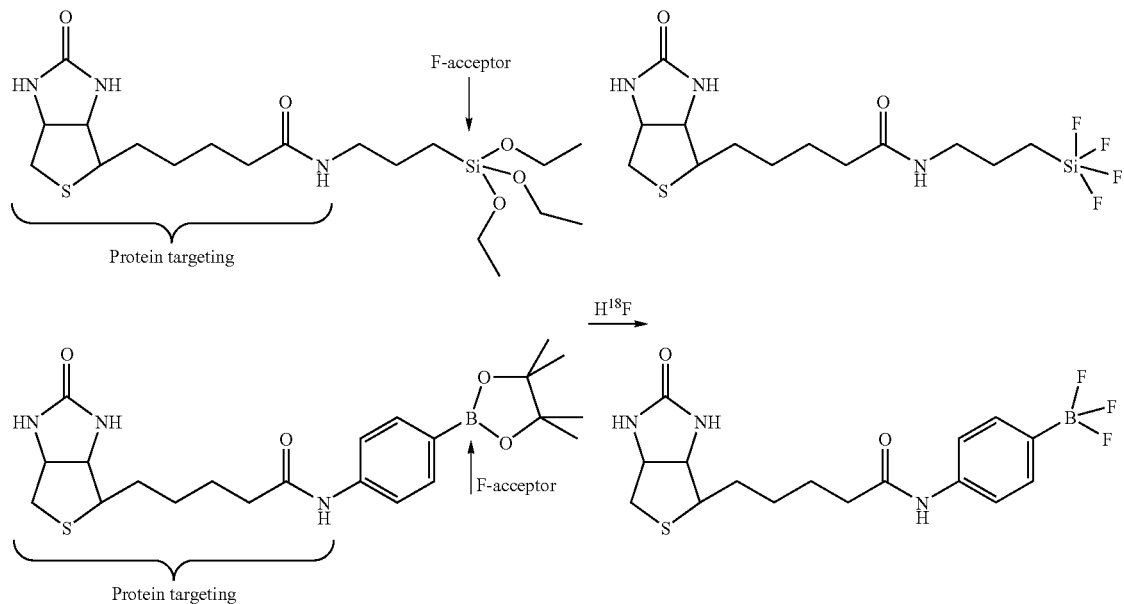

Scheme A

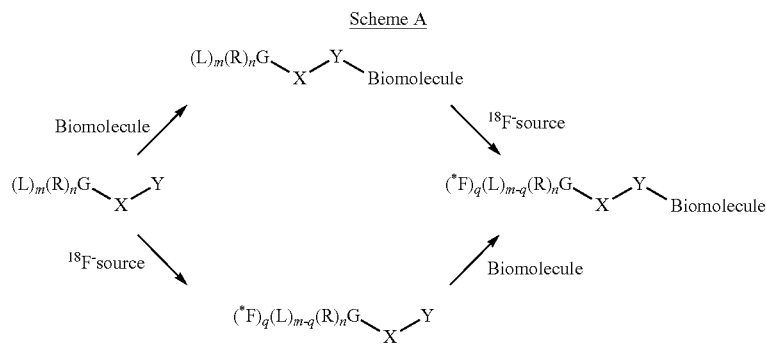

$^{18}$F fluorination may also be carried out in a precursor linked to a solid support or surface presenting a diol functionality (e.g. dextran, sephadex, polymerized/crosslinked starch, paper, cellulose, or any diol that is modified with a small tight binding ligand (e.g. biotin) that can be captured by a large molecule receptor (e.g. avidin) that is affixed to a solid support) where the linkage between the conjugate and the solid support is a boronic ester linkage, or other related linkage to boron, for example a bidentate linkage. $^{18}$F Fluorination would promote release of the labeled tracer that would acquire the trifluoroborate component upon release. This may increase the specific radioactivity during $^{18}$F fluorination of the tracer and enhance purity of the $^{18}$F fluorinated/labeled form, leaving residual unlabeled species attached to a solid support. Examples of conditions and moieties for preparing biomolecules conjugated to the moieties, (also comprising solid support conjugates) are well known in the art (see, for example, Doubrovin, M., et al. (2004) *Bioconj. Chem.*, 15, 1376-1388; and Keana, J. F. W., et al. (1986) *J. Org. Chem.*, 51, 1641-1644).

Appending of a biomolecule to a silicate surface with a silane is common in the production of various biomolecule "chips" (e.g. gene chips, protein arrays, or small molecule arrays). The production often involves first silanizing a silicate (e.g. glass) surface with a silane (for example a triethoxysilane) resulting in displacement of an ethanolic portion and fixation of a silyl group to the silicate surface. The alkyl group of the silane may be appended with either an amino, thiol or carboxylic acid group that allows covalent linkage of the biomolecule to the chip. This technology is readily adopted to the present invention since release a silyl-linked biomolecule from the silicate surface by fluoride treatment, results in the production of a biomolecule linked to an fluorosilicate. In this case, the leaving group was the silanized silicate which may take the form (Si—O—)$_x$. Accordingly, $^{18}$F Fluorination of the biomolecule may be achieved by linking a the biomolecule via a silicon or boron moiety to a solid support. For example, silicon-conjugated biomolecules, may be limited to a silicate (glass) surface, or to any surface or molecule presenting an alcohol (e.g. dextran, sephadex, polymerized/cross linked starch, paper, cellulose, or any alcohol (e.g. diol or triol) that is modified with a small tight binding ligand (e.g. biotin) that can be captured by a large molecule receptor (e.g. avidin) that is affixed to a solid support. Fluorination would promote release of the conjugate in labeled form (e.g. tetrafluorosilicate). This may increase the specific radioactivity during fluorination of the tracer and improve purity of the fluorinated composition, leaving residual unlabeled species attached to a solid support. The release of silyl-linked tracers from the surface by fluoride treatment, would result in the production of a tracer linked to an alkyl/aryl-tetrafluorosilicate. For example, tracers could be affixed to a solid surface via a trialkoxysilyl-treated surface, resulting in an alkyl/aryl-tetrafluorosilicate, which upon washing with $^{18}$F would result in release of the tracer from the surface to provide $^{18}$F-labeled tracers for imaging purposes. The Boron-conjugated biomolecules, for example, may be linked to a surface that present an alcohol (e.g. dextran, sephadex, polymerized/cross linked starch, paper, cellulose, or any alcohol (e.g. diol) that is modified with a small tight binding ligand (e.g. biotin) that can be captured by a large molecule receptor (e.g. avidin) that is affixed to a solid support).

Compositions for PET imaging according to this invention will comprise a suitable $^{18}$F in combination with a physiologically acceptable carrier. Toxicity of PET imaging agents is generally of minimal concern in view of the minute amounts of the radionuclide containing agent required in order to carry out imaging or localization of a target within a living body. The physiologically acceptable carrier or excipient may be any such carrier, usually in aqueous solution, suitable for injection to a patient. Preferred compounds of this invention adapted for PET imaging are relatively stable in such solutions at or near physiological pH. In some embodiments, organic or other cosolvents intended to facilitate dissolution of a compound of this invention may also be employed in a PET imaging composition. PET imaging compositions for this invention may also comprise additional components intended to facilitate targeting within the body or delivery of the agent within the body, including liposomes, micelles, or other formulations intended to sequester the agent for a time period or until delivery to a target region of the body or to protect a biomolecule component of the imaging agent.

EXAMPLES

The following examples are illustrative of some of the embodiments of the invention described herein. These examples should not be considered to limit the spirit or scope of the invention in any way.

Example 1

The Synthesis and Stability of a F-Boron Composition

4-Ammoniumphenyl Trifluoroborate. A saturated solution of 4-(4,4,5,5-Tetramethyl-1,3,2-dioxaborolan-2-yl) aniline was made up in of methanol (300 μL, reagent grade). $^1$H NMR (400 MHz, MeOH-$d_4$) δ 7.45 (d, J=8 Hz, 2H), δ 6.62 (d, J=8 Hz, 2H), δ 4.84 (s, 2H), δ 1.28 (s, 12H). $^{11}$B NMR (400 MHz, MeOH-$d_4$, $BF_2OEt_2$ ref) δ 31.13 (s) Upon room temperature addition of an aqueous 48% HF solution (100 μL, 2.76 mmol), instantaneous formation of a white precipitate was observed. This white precipitate was filtered and washed three times with 300 μL of ethanol. The solid had a pH of 1 when dissolved in 300 μL water. $^1$H NMR (400 MHz, $D_2O$) δ 7.55 (d, J=8 Hz, 2H), δ 7.20 (d, J=8 Hz, 2H). $^{11}$B NMR (400 MHz, $D_2O$, $BF_2OEt_2$ ref) δ 3.57 (s). $^{19}$F NMR (300 MHz, $D_2O$, TFA ref) δ −53.52 (s) δ −65.57 (s). ESI (negative mode) m/z calcd for $C_6H_6BF_3N^-$ 160.0, found 159.8.

Example 2

The Construction of a Thiophilic Boronating Reagent

4-(2-Bromoacetamido (4,4,5,5-Tetramethyl-1,3,2-dioxaborolan-2-yl)Benzene (F)

4-(4,4,5,5-Tetramethyl-1,3,2-dioxaborolan-2-yl)aniline (100 mg, 0.46 mmol) was dissolved in $CH_2Cl_2$ (1 mL, dried over $CaH_2$). Bromoacetyl bromide (44 μl, 0.51 mmol) was added to this solution while stirring at room temperature. This solution was stirred at room temperature for an additional 30 min before being diluted with 9 mL more $CHCl_3$. The resulting mixture was washed three times with 10 mL of water. The final wash had a pH of 5.5. The organic layer was dried over sodium sulfate, filtered, and concentrated under vacuum. The resulting solid was a beige powder. $^1$H NMR (400 MHz, $CDCl_3$) δ8.24 (s, 1H), δ7.77 (d, J=8 Hz, 2H), δ 7.53 (d, J=8 Hz, 2H), δ 3.98 (s, 2H), δ 1.29 (s, 12H). $^{11}$B NMR (400 MHz, $D_2O$, $BF_2OEt_2$ ref) δ 31.36 (s).

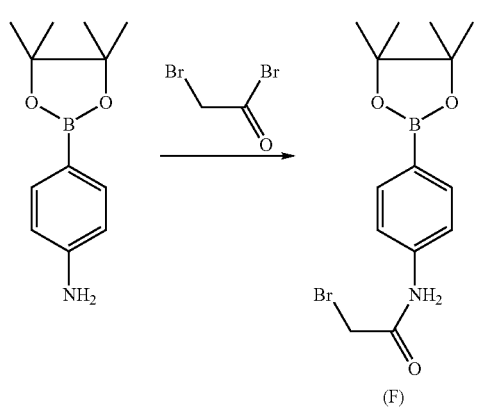

(F)

Example 3

Kinetic Protocol for Boron-Based $^{18}$F-DNA Labeling

Prior to $^{18}$F-labeling of the final DNA compound or other boron-based fluoride acceptors, dilute labeling conditions were developed for 4-(4,4,5,5-Tetramethyl-1,3,2-dioxaborolan-2-yl) aniline with cold $^{19}$F and the expectation that these labeling conditions can be extrapolated onto $^{18}$F studies. The general conditions established are as follows: 200 mM Acetic acid at pH 3.5, with 2 mM boron compound, and 20 mM $KHF_2$. In these conditions, between 2 and 3 fluorine atoms were transferred to the small boron molecule ($\phi BF_3$). $^{19}$F NMR (300 MHz, $D_2O$, TFA ref) δ −53.89 (s, $KHF_2$, 77% of fluorine integral), δ −62.50 (s, $\phi BF_3$, 33% of fluorine integral).

Spectroscopic studies showed a protecting group hydrolysis rate of 0.66±0.04 $min^{-1}$ in these conditions. Kinetics of fluorination in 100 mM Acetic acid at pH 3.5 showed that the rate of fluorination was 2.8±0.3 $min^{-1}$ in these conditions. The persistence of a $^{19}$F NMR peak near δ −66 despite a 20 mM boric acid chase, or in fluorination in the presence of 20 mM boric acid indicates that the B—F $\phi BF_3$ bond is stable. Fluorination after a 20 mM boric acid chase (chase at 1 h, NMR taken at 2 h): $^{19}$F NMR (300 MHz, $D_2O$, TFA ref) δ −50.23 (fluorine-boric acid species #1), δ−53.89 ($KHF_2$), δ −62.3 (fluorine-boric acid species #2), δ −66.30 (s, $\phi BF_3$). Fluorination in the presence of boric acid: $^{19}$F NMR (300 MHz, $D_2O$, TFA ref) δ −50.02 (fluorine-boric acid species #1), δ −52.47 ($KHF_2$), δ −62.0 (fluorine-boric acid species #2), δ −65.65 (s, $\phi BF_3$).

Example 4

The Synthesis of a Boron Containing Biotin Conjugate (A)

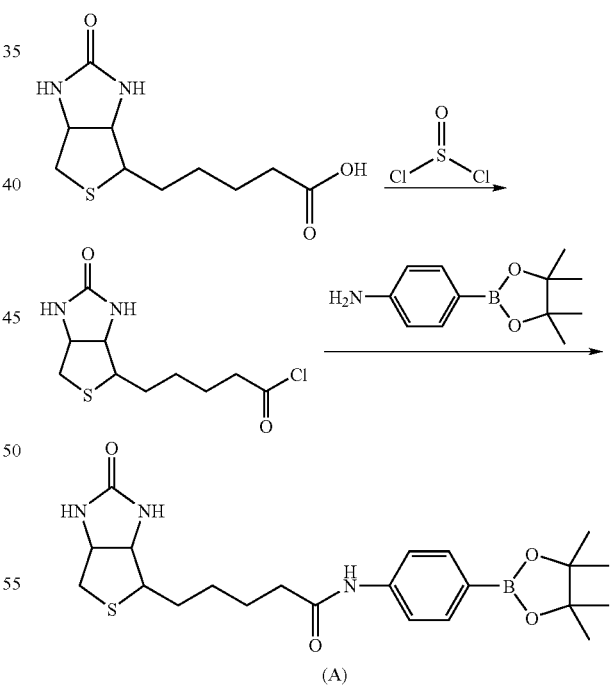

(A)

(A) A flame dried 50 ml round bottom flask was charged with a magnetic stirrer and 110 mg (0.44 mmol) of d-biotin. 2 ml of neat excess thionyl chloride was added to the stirring solution. The reaction was allowed to proceed for 20 min. Excess thionyl chloride was removed under vacuum. The resulting brown oil was resuspended in 25 ml of chloroform and dried down to ensure the complete removal of thionyl chloride. The resulting residue was resuspended in 2 ml of acetonitrile and a solution of 96 mg (0.44 mmol) of 4-(4,4,5,5-tetramethyl-1,3,2-dioxaborolan-2-yl)aniline in 2 ml of acetonitrile was added. The reaction was allowed to proceed for 20 min before 50 ml of diethyl ether was added, forming a precipitate that was collected by decanting. This precipitate was suspended in 10 ml of chloroform, which was washed three times with 10 ml of water and, dried over anhydrous sodium sulphate. Filtration gave (A). ESI$^+$ (in MeOH): =446.1 MH$^+$ found (446.28 Calculated), 468.0 MNa$^+$ found (468.21 Calculated), 913.3 M$_2$Na$^+$ found (913.43 Calculated). $^1$H NMR also confirmed the presence of product.

Example 5

The Synthesis of a Silane Containing Biotin Conjugate (B)

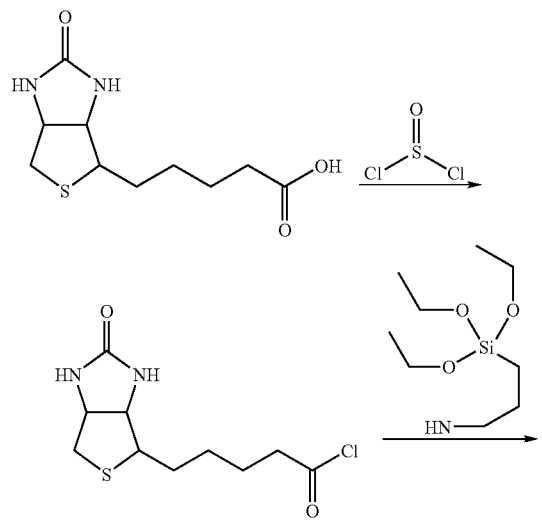

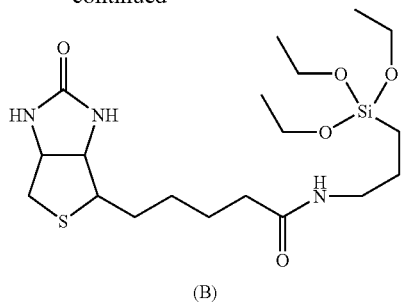

(B)

(B) A flame dried 50 ml round bottom flask was charged with a magnetic stirrer and 550 mg (2.25 mmol) of d-biotin. 10 ml of neat thionyl chloride was added to the stirring solution and reaction was allowed to proceed for 20 min. Excess thionyl chloride was removed under vacuum. The resulting brown oil was resuspended in 25 ml of methylene chloride and dried down again to ensure the removal of thionyl chloride. 5 ml of methylene chloride was added to the resulting oil followed by the addition of 25 ml of diethyl ether. The formation of a precipitate was observed. This solution was concentrated again to ensure the quantitative removal of thionyl chloride. To the resulting concentrated oil, 4 ml (17 mmol) of 3-aminopropyltriethoxysilane and 25 ml of methylene chloride was added. This addition guaranteed complete solubilization of the reaction mixture. Precipitation was observed within the first 10 min of the reaction. The crystals of (B) were filtered off through a glass wool plug. The supernatant was collected, evaporated, resuspended in 5 ml of methylene chloride, and (B) was precipitated out with 50 ml of diethyl ether. (B) was collected by filtration, washed with 100 ml of diethyl ether and placed under vacuum. ESI$^-$ (in MeCN): =482.3 MCl$^-$ found (482.19 Calculated). $^1$H NMR also confirmed the presence of product.

Example 6

The Synthesis of a Boron Containing Folate Conjugate (E)

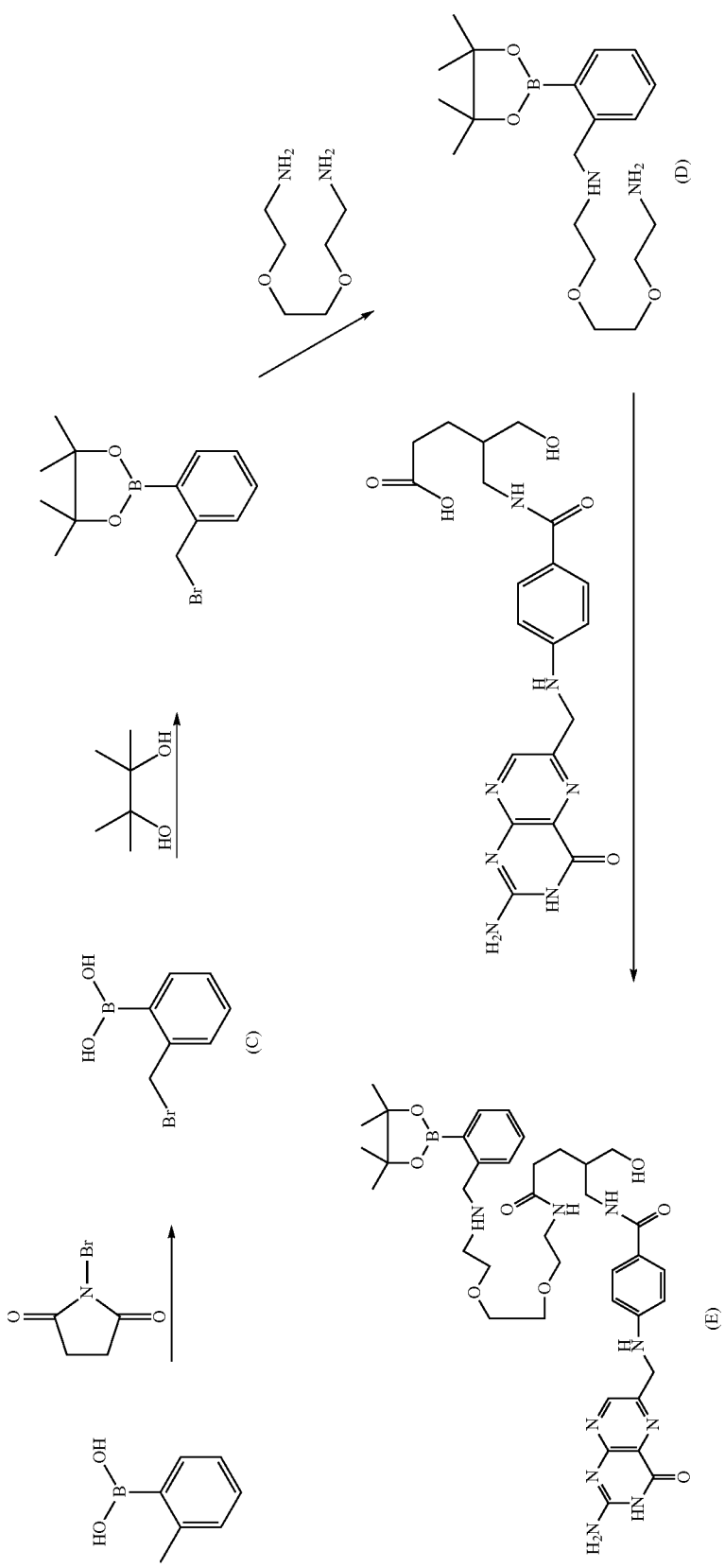

(C) A 500 ml round bottom flask was charged with a magnetic stirrer, 250 ml of benzene, and 5.02 g (37 mmol) of o-toluyl-boronic acid. To the stirring suspension at room temperature, 7.77 g (43 mmol) of powdered N-bromosuccinimide and 0.792 g (4.8 mmol) of 2,2'azobis(2-methyl-propionitrile) were added. Full solubility of the reaction mixture was subsequently observed. The reaction was refluxed for 2 hours. A precipitate was observed upon cooling of the reaction to room temperature. The precipitate was filtered off and the benzene supernatant was washed three times with 200 ml of water before being dried over anhydrous sodium sulfate. Following filtration and concentration, 3.42 g (16 mmol, 43% yield) of (C) was isolated. $^1$H NMR confirmed the presence of product.

(D) A 15 ml conical polypropylene tube was charged with 200 mg (0.93 mmol) of compound (C) and approximately 1.5 ml of excess solid pinacol alcohol. The charged conical tube was placed in a 30-40° C. water bath for 10 min in order to melt the pinacol alcohol and allow reaction. The reaction mixture was subsequently transferred to a separatory funnel where it was washed three times with 20 ml of water, and dried over anhydrous sodium sulphate. The sodium sulphate was filtered off, and the resulting solution was concentrated in a 25 ml round bottom flask. This concentrate was resuspended with 2 ml of chloroform and 4.5 ml (30.1 mmol) of excess neat 2,2'ethylenedioxybisethylamine. The mixture was vortexed and allowed to react at room temperature for 30 min. Following reaction, 100 ml of diethyl ether was added to the reaction to afford a pale yellow precipitate. This precipitate was centrifuged to an oil that was collected, resuspended in 25 ml of methylene chloride, washed twice with 25 ml of SM NaOH, twice with 25 ml of water and dried over anhydrous sodium sulphate. A pure sample of (D) was isolated upon filtration and concentration. ESI$^+$ (in MeOH): =365.2 MH$^+$ found (365.26 Calculated). $^1$H NMR also confirmed the presence of product.

(E) In a 15 ml conical tube, 300 mg (0.67 mmol) of folic acid was dissolved in 12 ml of DMSO. 126 mg (0.67 mmol) of EDC and (0.67 mmol) of (D) were added as powders to this solution. The reaction was allowed to proceed for 24 hours at room temperature. The product was precipitated out of the reaction with 100 ml of a 30% acetone 70% diethyl ether solution, collected by filtration, and washed again with 100 ml of the 30% acetone 70% diethyl ether solution. Thin layer chromatography confirmed the formation of product.

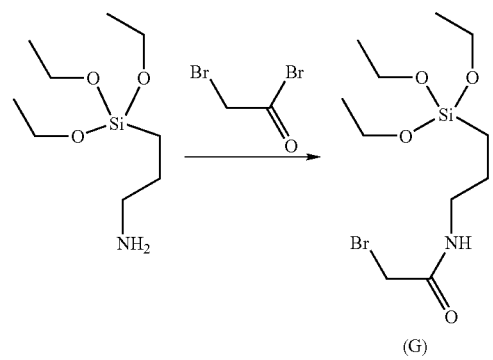

(G)

Example 7

The Synthesis of a Silane Containing Electrophile (G) for Labeling Biomolecules (G) A 50 ml round bottom flask was charged with a stir bar, 10 ml of chloroform, and 0.440 ml (5.0 mmol) of bromoacetyl bromide. To this stirring solution, 1.1 ml (4.7 mmol) of 3-aminopropyltriethoxysilane was added. The resulting precipitate is filtered off and the supernatant is concentrated under high vacuum. $^1$H NMR confirmed the presence of product.

(C), (F), and (G), can be reacted with many nucleophiles in aqueous or organic conditions in order to label the desired nucleophile with the described boronic ester or silane. Nucleophiles that are contemplated include thiols, amines, imidazoles. The use of thiophosphates has been specifically employed to label DNA. The described tags themselves and the labeling method are examples. There are numerous variations to this method and alternatives to the chemistry proposed for labeling biomolecules with Si or B.

Example 8

The Synthesis of Boron Containing Phosphoramidites for Use in the Preparation of Boron Containing DNA (L) and (N)

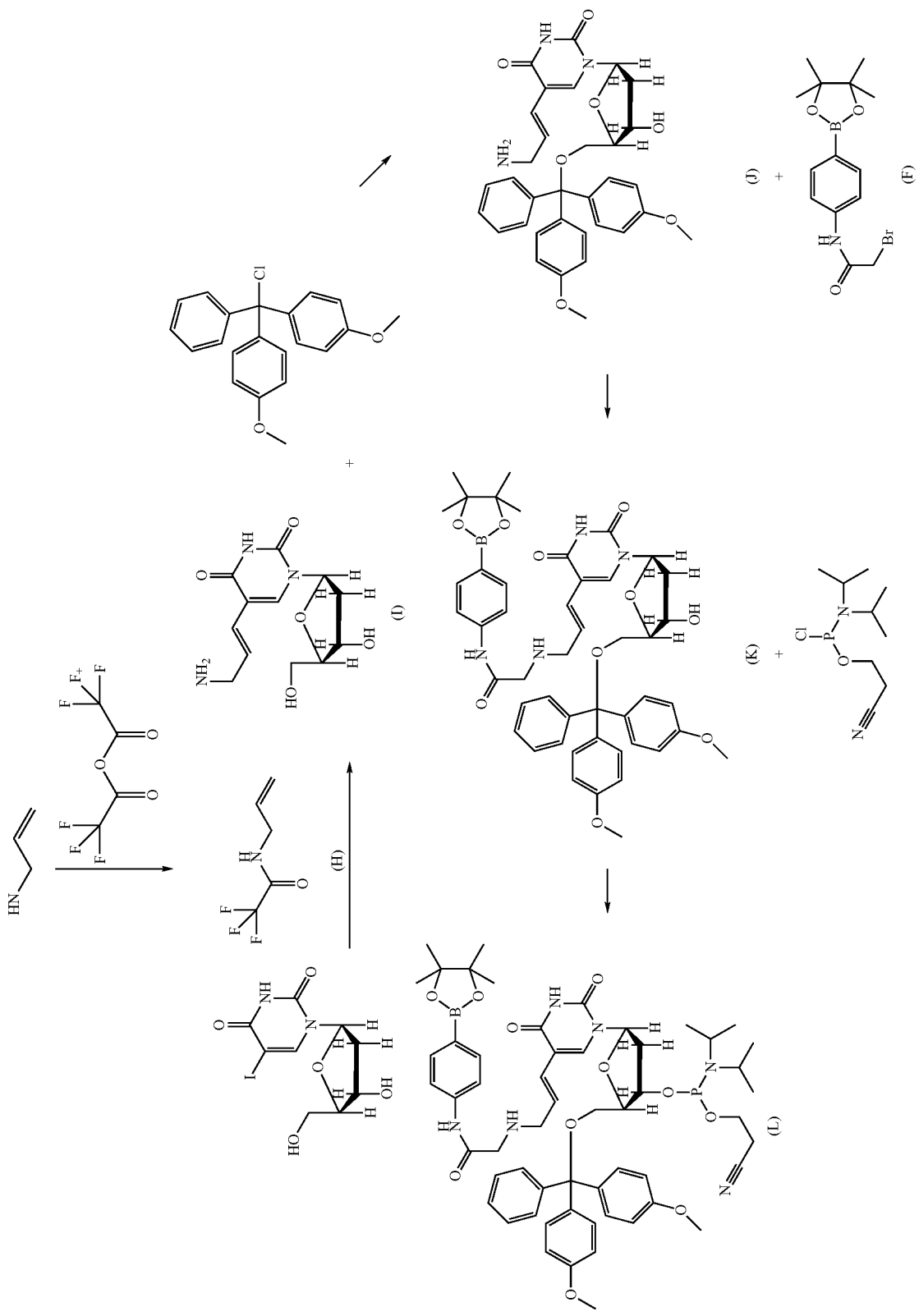

(H) A flame dried 250 ml round bottom flask containing a magnetic stirrer was flushed with nitrogen gas and charged with 42.7 mg (569 mmol) of allylamine. 40.0 ml (0.282 mmol) of neat trifluoroacetic anhydride was added to the stirring reaction by syringe pump. The reaction was allowed to proceed for 24 hours. (H) was collected by vacuum distillation (b.p. 75° C., 5.3 mm Hg). $^1$H NMR confirmed the presence of product.

(I) A 250 ml round bottom flask was charged with a magnetic stirrer, 3.5 g (9.88 mmol) of (+)-5-iodo-2'-deoxyuridine, and 125 ml of 0.1 M sodium acetate buffer at pH 5.2. The suspension was heated to 60° C. in order to completely dissolve (+)-5-iodo-2'-deoxyuridine. The clear solution was cooled to room temperature and 9.65 g (63.1 mmol) of (H) was added. 2.91 g (9.89 mmol) of sodium tetrachloropalladate-II was added and the reaction was allowed to proceed overnight. The reaction was filtered through celite, concentrated and resolved by flash chromatography on silica with 100% ethyl acetate as the running solvent. The fractions containing the trifluoroacetate-protected derivative of (I) was concentrated under vacuum. In a 50 ml round bottom flask, 1.2 g (1.72 mmol) of this compound was dissolved in 9 ml of ethanol, and 18 ml of conc. ammonium hydroxide was added. This reaction was allowed to proceed for 12 hours before it was concentrated. The concentrate was columned on silica with a gradient of 2% methanol and 0.3% triethylamine in 97.7% chloroform to 4% methanol and 0.3% triethylamine in 95.7% chloroform. The fractions containing (I) were concentrated under vacuum. $^1$H NMR confirmed the presence of product.

(J) A flame dried 100 ml round bottom flask was charged with a magnetic stirrer, 1.89 g (4.98 mmol) of (I), 50 ml of chloroform, and 2.5 ml (17.95 mmol) of triethylamine. 4.22 g (12.46 mmol) of dimethoxytritylchloride was added to the stirring solution as a powder. The reaction was allowed to proceed for 30 min before it was concentrated under vacuum. The reaction concentrate was precipitated and washed twice with 125 ml of hexanes. The remaining solid was flash chromatographed on silica with 100% ethyl acetate as the running solvent. The fractions containing (J) were concentrated under vacuum. $^1$H NMR confirmed the presence of product.

(K) A 100 ml round bottom flask was charged in the following order with a magnetic stir bar, 900 mg (1.54 mmol) of (J), 50 ml of chloroform, and 0.64 ml of triethylamine (4.61 mmol). The reaction was initiated by the addition of 626 mg (1.846 mmol) of solid (F) to the stirring mixture. The reaction was allowed to proceed for 16 hours before it was transferred directly to a separatory funnel and washed twice with 150 ml of water. The organic layer was dried over anhydrous sodium sulphate, filtered, and concentrated to an oil. Addition of 75 ml of diethyl ether to this oil afforded a pale yellow precipitate. This precipitate was collected and washed twice with ether. Analysis by $^1$H NMR confirmed that (K) was present in a pure state, and that further workup was not necessary. ESI$^+$ (in MeOH): =845.4 MH$^+$ found (845.39 Calculated).

(L) A flame dried 50 ml round bottom flask was flushed with nitrogen gas, charged with a magnetic stirrer and 900 mg (1.066 mmol) of (K). A 9:1 solution of dry methylene chloride: dry pyridine was added to the solid, and the solution was placed under vacuum for 12 hours to quantitatively remove water. The resulting oil was placed in a nitrogen atmosphere and 5 ml of dry methylene chloride, 0.743 ml (4.264 mmol) of diisopropylethylamine and 0.713 ml (3.198 mmol) of 2-cyanoethyl diisopropylchlorophosphoramidite was added with stirring. The reaction was allowed to proceed for 1 hour before 15 ml of chloroform was added. The dilute solution was transferred to a separatory funnel, washed twice with 20 ml of water, dried over anhydrous sodium sulphate, filtered, and concentrated to a yellow foam. $^{32}$P and $^1$H NMR confirmed the presence of product. ESI$^+$ (in MeOH): =1045.6 MH$^+$ found (1045.50 Calculated). 1067.6 MNa$^+$ found (1067.48 Calculated).

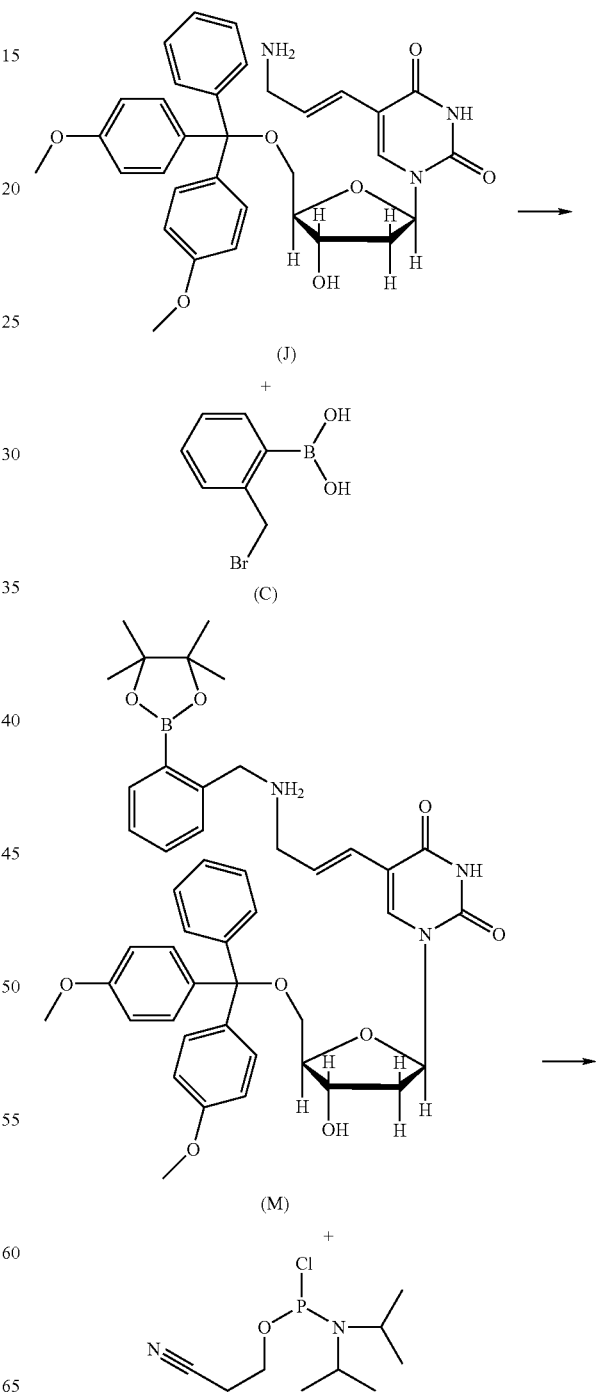

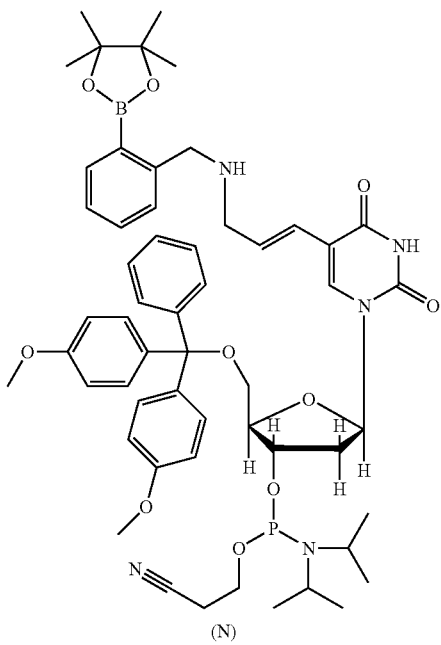

(N)

(M) A 15 ml conical polypropylene tube was charged with 600 mg (2.79 mmol) of compound (C) and approximately 4.5 ml of excess solid pinacol alcohol. The charged conical tube was placed in a 30-40° C. water bath for 10 min in order to melt the pinacol alcohol and allow reaction. The reaction mixture was subsequently transferred to a separatory funnel where it was washed three times with 20 ml of water, and dried over anhydrous sodium sulphate. The sodium sulphate was filtered off, and the resulting solution was concentrated in a 25 ml round bottom flask. 500 mg (1.68 mmol) of this solid was added to a 50 ml round bottom flask containing a magnetically stirred solution of 820 mg (1.40 mmol) of (J), 20 ml of chloroform, and 0.714 ml of triethylamine (5.13 mmol). This reaction was allowed to proceed for 48 hours before it was transferred to a separatory funnel and washed three times with 75 ml of water. The organic layer was dried over anhydrous sodium sulphate, filtered, and concentrated to a solid. Analysis by $^1$H NMR confirmed that (M) was present in a 80% pure state, further workup was not performed. ESI$^+$ (in MeOH): =802.5 MH$^+$ found (802.39 Calculated).

(N) A flame dried 50 ml round bottom flask was flushed with nitrogen gas, charged with a magnetic stirrer and 1.29 g (1.64 mmol) of (M). A 9:1 solution of dry methylene chloride: dry pyridine was added to the solid, and the solution was placed under vacuum for 12 hours to quantitatively remove water. The resulting oil was placed in a nitrogen atmosphere before 30 ml of dry methylene chloride, 1.0 ml (5.74 mmol) of diisopropylethylamine and 0.73 ml (3.28 mmol) of 2-cyanoethyl diisopropylchlorophosphoramidite was added with stirring. The reaction was allowed to proceed for 1 hour before the solution was transferred to a separatory funnel, washed three times with 30 ml of 5% sodium bicarbonate, dried over anhydrous sodium sulphate, filtered, and concentrated to a yellow foam. $^{32}$P and $^1$H NMR confirmed the presence of product. ESI$^+$ (in MeOH): =1002.8 MH$^+$ found (1002.5 Calculated).

Example 9

The Synthesis of a Boron-Modified DNA Oligonucleotide Through Solid Phase Strategies The building blocks (L) and (N) have be used to incorporate boron into DNA on large scale (1 micromole) using standard automated solid-phase methods on solid phase DNA synthesizers.

The 5' thiophosphorylated nucleophilic oligonucleotide, 5'-TTTTCTTTTCCCCCC-3' (SEQ ID NO: 1), was synthesized using standard automated solid-phase methods on applied Biosystems DNA synthesizers. 20 µL of an aqueous solution of this oligonucleotide (20 nmol) was added to 3.6 µl of an aqueous solution of tris(2-carboxyethyl)-phosphine HCl (100 nmol) adjusted to pH 7.0 with triethylamine and the reaction mixture was mixed to allow reduction of any disulfide bonds that had occurred and to prevent any formation of disulfide during the subsequent alkylation reaction. The addition of tris(2-carboxyethyl)-phosphine HCl was often omitted without consequence in terms of yield. Following optional tris(2-carboxyethyl)-phosphine HCl addition, 100 nmol of (F) or (G) was added. This mixture was allowed to sit at room temperature for 16 hours. Following reaction, the mixture was desalted over a G-25 spin column. Extent of alkylation was evaluated by 20% Urea-PAGE followed either via UV shadowing or by use of a radiolabeled oligonucleotides and phosphoimaging (autoradiography). Purification of the boron-labeled oligonucleotide was achieved by drying down the desalted oligonucleotide and resuspending it in 30 µl of a 10 mM EDTA (pH 8), 95% formamide, 4% H$_2$O, 0.5% bromophenol blue, and 0.5% xylene cyanol, then loading the solution onto a 7 M urea 20% 29:1 bis:acrylimide polyacrylamide gel. DNA was imaged through UV shadowing and eluted from gels by using the crush and soak method with 1% LiClO$_4$/0.7 mM NEt$_3$. The eluant was dried, resuspended in water and precipitated with 1% LiClO$_4$ in acetone The precipitates were washed twice with ethanol before being desalted over a G-25 spin column.

Confirmation and extent of labeling and stability of the boron linkage was analyzed by $^{32}$P-labeling the boron containing oligonucleotide with terminal transferase and α-$^{32}$P ddATP. PAGE analysis of this reaction revealed that more than 80% of the thiophosphate oligonucleotide was converted to the boron labeled oligonucleotide. The relative mobility of the $^{32}$P-labeled boronated oligonucleotide was retarded when run with a $^{32}$P-labeled thiophosphate oligonucleotide control, confirming positive boron labeling of the oligonucleotide.

Example 10

Boron- and Silica-Based $^{18}$F-Labeling of Biotin 300 nmol to 1 nmol of unmodified (d)-biotin (negative control), Boron-modified Biotin (A), or Silicon-modified Biotin (B), were dried down in eppendorf tubes and bought up in 5 µL of either MeOH, DMF, THF or water. The value of pH was adjusted to 4.5 with 1 µL of a 1000 mM Acetic acid buffer at pH 4.2. Aqueous $^{18}$F with a specific activity of 52.2 mCi/1000 µL measured at 11:00 AM was added to a stock solution of a KHF$_2$ at a noted concentration. 3 µl of these standard KHF$_2$ solutions containing the required equivalents of F anion in water (3.3 for the boron experiment, and 4.4 for the silica and control experiments) were added to each mixture between 12:05 and 12:20 PM. The reacting volume was 10 µL, thus boron, silicon, and unmodified biotin concentrations varied from 30 mM to 1 mM.

At 1:10 PM, 100 μL of 300 mM NaHCO$_3$, pH 7-8 was added to each tube to neutralize the solution. A volume of 6.8 μL of Roche Streptavidin magnetic particles, with an estimated binding capacity of >3.5 pmol Biotin/μL that was given by the Roche Scientific, that had been prewashed with 10 mM NaHCO$_3$, pH 7-8, 1 M NaCl and 1 mM EDTA, was added to each solution. These beads were magnetized and washed 3 times with 100 μL of 10 mM Carbonate Wash buffer (10 mM NaHCO$_3$ pH 7-8, 1 M NaCl, 1 mM EDTA)(Wash #1 was started at, 2:06 PM, Wash #2 2:28 PM, and Wash #3 2:50 PM). Beads were finally suspended in 5 μL of water and spotted on a silica plate. The plate was allowed to dry and then was taped with cellophane tape to retain particles.

The silica plate was exposed to a phosphorimager screen for 18 h. Boron and silica containing compounds were $^{18}$F labeled with almost quantitative transfer efficiency. The biotin control was not $^{18}$F labeled.

Example 11

Boron-Based $^{18}$F-Biotin Labeling of Boron Containing DNA

Noted quantities of DNA that had been synthesized with (L) or (N) were incubated in water containing trace $^{18}$F. These solutions were immediately reacted with 3 equivalents of F anion in the form of KHF$_2$, or HF. Adjustment of pH took place upon the addition of 17.9 mmol of acetic acid buffered at pH 4.5. Final reaction volumes were 10 μl. All lanes were quenched with 10 μL of the load solution prior to being loaded on denaturing polyacrylamide gels used for resolving free $^{18}$F away from DNA. Load solution consisted of 99% formamide 0.5% XC+BOB and no EDTA. Gels were 20% polyacrylamide 29:1 monomer:bis, 7 M urea containing 40 mM Tris acetate with no EDTA added. Resolution of samples within the gel involved applying current at 12 W for 3 hours. The phosphoimages used to detect $^{18}$F, show bands that overlay exactly with UV shadow images that indicate location of the oligonucleotide, indicating stable $^{18}$F bond formation with the boron containing oligonucleotide.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

What is claimed is:

1. A compound of the formula:

$$(F)_m G(R)_n$$

wherein
each R is a group comprising at least one carbon, nitrogen, phosphorus or sulfur atom and G is joined to R through said carbon, nitrogen, phosphorus or sulfur atom;
G is silicon or boron;
m is 2 to 5 and n is 1 to 3 with m+n=3 to 6 when G is silicon;
m is 1 to 3 and n is 1 to 3 with m+n=3 to 4 when G is boron;
and wherein the compound further comprises one or more counterions when the above formula is charged; and wherein at least one F is $^{18}$F.

2. The compound of claim 1 wherein one or more counterions are present when m+n=5 or 6 and G is Si and when m+n=4 and G is B.

3. The compound of claim 1 wherein G is silicon.

4. The compound of claim 3 wherein at least two of F are $^{18}$F.

5. The compound of claim 3 wherein:
(i) m=2, n=3;
(ii) m=4, n=1;
(iii) m=5, n=1;
(iv) m=2, n=2;
(v) m=3, n=1; or
(vi) m=3, n=2.

6. The compound of claim 5 wherein:
(i) m=2 and n=3;
(ii) m=4 and n=1; or
(iii) m=5 and n=1.

7. The compound of claim 5 wherein m=4, n=1.

8. The compound of claim 1 wherein G is boron.

9. The compound of claim 8 wherein:
(i) m=1, n=3;
(ii) m=2, n=2;
(iii) m=3, n=1;
(iv) m=1, n=2; or
(v) m=2, n=1.

10. The compound of claim 9 wherein:
(i) m=1 and n=3;
(ii) m=2 and n=2; or
(iii) m=3 and n=1.

11. The compound of claim 1 wherein each R is joined to G through a nitrogen or carbon atom.

12. The compound of claim 1 wherein each R is joined to G through a carbon atom.

13. The compound of claim 1 wherein G is silicon and at least one R is selected from the group consisting of: aryl,

SEQUENCE LISTING

<160> NUMBER OF SEQ ID NOS: 1

<210> SEQ ID NO 1
<211> LENGTH: 15
<212> TYPE: DNA
<213> ORGANISM: Artificial
<220> FEATURE:
<223> OTHER INFORMATION: Synthetic

<400> SEQUENCE: 1
ttttcttttc ccccc     15 amino, methyl, phenyl, aminophenyl, aminomethylphenyl, alkoxymethylphenyl, a porphyrin, a porphyrin derivative and a biomolecule.

14. The compound of claim 1 wherein G is boron and at least one R is selected from the group consisting of: aryl, amino, phenyl, methyl, aminophenyl, aminomethylphenyl, alkoxymethylphenyl, and a biomolecule.

15. The compound of claim 1 wherein at least one R is a moiety capable of bonding to a biomolecule.

16. The compound of claim 1 wherein at least one R is a biomolecule.

17. The compound of claim 16 wherein the biomolecule is a sugar, a peptide, a nucleic acid or derivative or analog thereof.

18. The compound of claim 16 wherein the biomolecule is a hormone, somatostatin, growth hormone, VEGF, EGF, an antibody, a breast cancer antigen specific antibody, a prostate cancer antigen specific antibody, a melanoma antigen specific antibody, a ligand, a RGD-motif ligand recognizing a matrix metalloprotease, an aptamer, an aptamer recognizing a cell surface protein, folic acid, a folic acid derivative and a methotrexate or a derivative or analog thereof.

19. A compound according to claim 1 comprising more than one $^{18}F$ atom.

20. A compound according to claim 1 wherein m is at least 2 and at least one F is $^{19}F$.

21. A compound of the formula:

$(F)_m G(R)_n$ wherein
each R is a group comprising at least one carbon, nitrogen, phosphorus or sulfur atom and G is joined to R through said carbon, nitrogen, phosphorus or sulfur atom;
at least one R is an aryl group;
G is silicon or boron;
m is 2 to 5 and n is 1 to 3 with m+n=3 to 6 when G is silicon;
m is 1 to 3 and n is 1 to 3 with m+n=3 to 4 when G is boron;
and wherein the compound further comprises one or more counterions when the above formula is charged; and wherein at least one F is $^{18}F$.

22. The compound of claim 21, wherein the aryl group is selected from the group consisting of:

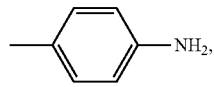

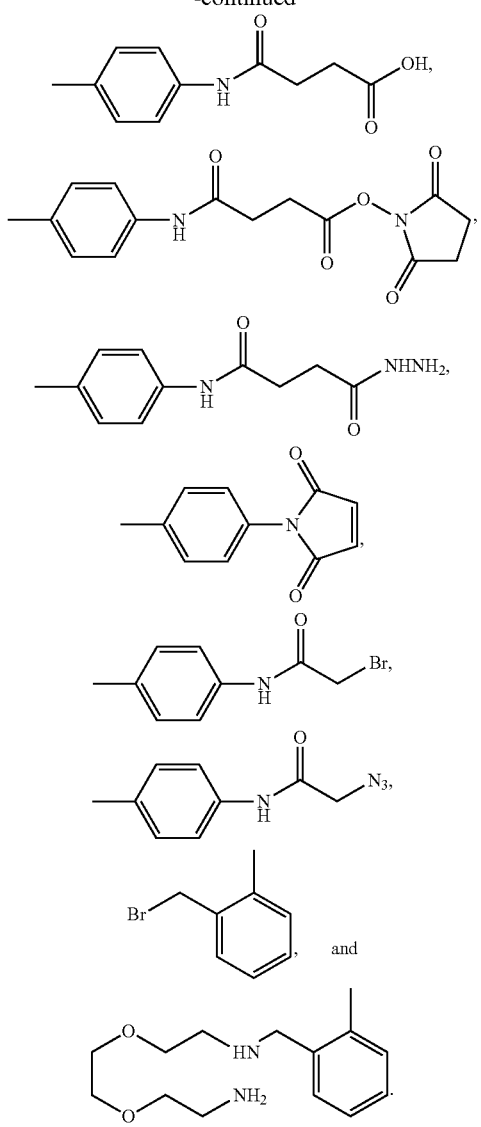

* * * * *